United States Patent
Wolf

(10) Patent No.: US 10,386,296 B1
(45) Date of Patent: Aug. 20, 2019

(54) SYSTEMS AND METHODS FOR DETERMINATION AND APPLICATION OF NITROGEN FERTILIZER USING CROP CANOPY MEASUREMENTS

(71) Applicant: Arable Labs, Inc., Princeton, NJ (US)

(72) Inventor: Lawrence Adam Wolf, Princeton, NJ (US)

(73) Assignee: Arable Labs, Inc., Princeton, NJ (US)

( * ) Notice: Subject to any disclaimer, the term of this patent is extended or adjusted under 35 U.S.C. 154(b) by 0 days.

(21) Appl. No.: 16/212,105

(22) Filed: Dec. 6, 2018

Related U.S. Application Data

(60) Provisional application No. 62/595,111, filed on Dec. 6, 2017.

(51) Int. Cl.
| | | |
|---|---|---|
| *G01N 21/00* | (2006.01) | |
| *G01N 21/25* | (2006.01) | |
| *G01N 33/02* | (2006.01) | |
| *G01N 21/17* | (2006.01) | |

(52) U.S. Cl.
CPC ......... *G01N 21/255* (2013.01); *G01N 33/025* (2013.01); *G01N 2021/1797* (2013.01)

(58) Field of Classification Search
CPC combination set(s) only.
See application file for complete search history.

(56) References Cited

U.S. PATENT DOCUMENTS

| | | | |
|---|---|---|---|
| 6,393,927 B1 | 5/2002 | Biggs et al. | |
| 9,841,533 B2 | 12/2017 | Wolf et al. | |
| 9,939,319 B2 | 4/2018 | Wolf et al. | |
| 10,012,767 B2 | 7/2018 | Wolf et al. | |
| 10,156,475 B2 | 12/2018 | Wolf et al. | |
| 2016/0169855 A1* | 6/2016 | Baity ................ | G01N 33/24 47/58.1 SC |
| 2018/0180768 A1 | 6/2018 | Wolf et al. | |
| 2018/0284323 A1 | 10/2018 | Wolf et al. | |

OTHER PUBLICATIONS

Sellers, P.J., Canopy reflectance, photosynthesis and transpiration, International Journal of Remote Sensing, 6:8, 1335-1372, DOI: 10.1080/01431168508948283,1985; 39 pages.

Gitelson, Anatoly A. et al., Synoptic Monitoring of Gross Primary Productivity of Maize Using Landsat Data, IEEE Geoscience and Remote Sensing Letters, vol. 5, No. 2, Apr. 2008; 5 pages.

Gitelson, Anatoly A. et al., Use of a Green Channel in Remote Sensing of Global Vegetation from EOS-MODIS, Remote Sensing of Environment 58:289-298, Elsevier Science Inc., 1996; 10 pages.

Ustin, Susan L. et al., Retrieval of foliar information about plant pigment systems from high resolution spectroscopy, Remote Sensing of Environment 133, Supplement 1 (Sep. 2009; Imaging Spectroscopy Special Issue), pp. S67-S77, DOI: 10.1016/j.rse.2008/10.019, 2009; 13 pages.

\* cited by examiner

*Primary Examiner* — Abdullahi Nur
(74) *Attorney, Agent, or Firm* — Ulmer & Berne LLP

(57) ABSTRACT

Fertilizer application is challenged by inadequate constraints on key factors that determine how much to apply, and when to apply. Systems and methods for are disclosed that can make use of prior information (e.g. from field trials), time series data from a radiation measuring device, and episodic but spatially extensive satellite data, to constrain these uncertainties.

24 Claims, 13 Drawing Sheets

SYSTEMS AND METHODS FOR DETERMINATION AND APPLICATION OF NITROGEN FERTILIZER USING CROP CANOPY MEASUREMENTS

CROSS-REFERENCE TO RELATED APPLICATIONS

This application claims the benefit of U.S. patent application Ser. No. 62/595,111, entitled SYSTEMS AND METHODS FOR DETERMINATION AND APPLICATION OF NITROGEN FERTILIZER USING CROP CANOPY MEASUREMENTS, filed on Dec. 6, 2017, the disclosure of which is incorporated herein by reference in its entirety.

BACKGROUND

The strong relationship between nitrogen availability in soil and crop yields is well known in the art. Of the major plant nutrients (N, P, K, Ca, Mg, and S), nitrogen is the nutrient required in the greatest quantities and much research has been conducted over the years to determine the nitrogen fertilizer requirements of crops. Applying too little nitrogen causes severe economic losses by reducing crop yields, while applying too much nitrogen is not only expensive but also causes harmful levels of $NO_3$ to leach into the ground and surface water supplies.

Determining the need for nitrogen is particularly difficult since most soil nitrogen is tied up in the soil organic matter and is unavailable to plants. The amount of nitrogen that is made available (in the form of $NO_3$ and $NH_4$) to plants during the growing season depends strongly on factors such as the previous cropping history of the field, soil organic matter content, microbial activity and rainfall (which quickly leaches the available forms of nitrogen away from the root zone). These difficulties have led some investigators to explore the use of plant nitrogen analysis instead of soil tests, since the plant itself should be a reliable indicator of the amount of nitrogen available to it.

Chemical assaying of plant nitrogen status is typically a slow and time consuming process because, as in the case of corn, about a dozen leaves are usually collected which must then be dried, ground, and analyzed using one of several laboratory techniques. Interpreting the laboratory data involves considerable uncertainty because leaf nitrogen concentrations decrease during the growing season and nitrogen concentrations further depend on which leaf is sampled. These difficulties led to efforts to develop rapid, non-destructive methods for assessing the nitrogen status of crops.

Crops that are well-supplied with nitrogen grow vigorously and look deep green in color due to their high leaf chlorophyll concentrations, while crops deficient in nitrogen grow less well and look yellow-green (chlorotic) due to low concentrations of chlorophyll. This led to the development of a device for measuring leaf chlorophyll content, called a chlorophyll meter, which measures light transmittance through individual leaves in the red (approximately 670 nm) and near-infrared (approximately 800 nm) regions of the electromagnetic spectrum. Furthermore, above a certain level of nitrogen fertilizer application, crop growth and chlorophyll content reach a plateau or a maximum, referred to hereinafter as the nitrogen fertilizer response plateau. This permits the use of a reference strip which provides a baseline against which nitrogen stress can be measured. However, due to the fact that a very great number of leaf measurements must be taken in order to survey an entire field for variable rate fertilizer adjustments, this method has not been widely accepted in commercial agriculture.

An additional problem with leaf chlorophyll or leaf color measurements is that the difference in leaf chlorophyll (or color) between a nitrogen deficient plant and a nitrogen sufficient plant is relatively small. By the time nitrogen fertilizer deficiency has caused a detectable change in leaf color, significant and unrecoverable yield reductions have already taken place. Therefore, leaf chlorophyll measurements using leaf transmittance have to be very precise, requiring measurements to be done under controlled illumination and light-path geometry. Measurements must be done on individual leaves clamped within an instrument. It is not possible at present to measure the entire crop canopy chemical attributes (color, chlorophyll or nitrogen concentration) with sufficient precision to be of value for detecting nitrogen deficiencies before irretrievable losses have already taken place. Measuring entire crop canopy reflectance in the green band does not measure leaf greenness (i.e. color), it merely measures the reflection in the green band of contrasting targets within the field of view of the sensor (plants, soil and shadows). Using chlorophyll fluorescence is even more problematic because fluorescence is not only a function of nitrogen status and leaf chlorophyll content but also depends on the short-term changes in the plant's metabolic pathways. Fluorescence is a very unstable physiological parameter which varies from hour to hour with illumination, drought and a variety of other stresses. It is difficult to see how it could be used for determining the nitrogen needs of a field crop.

A more sensitive alternative to measuring color change is to measure changes in standing crop biomass or some other physical attribute such as leaf area, crop density, crop cover, etc. Measuring the entire crop canopy physical attributes is radically different from and has several advantages over measuring individual leaf chemical attributes such as chlorophyll content or color. Changes in standing crop density, for example, show a greater sensitivity to nitrogen supply than do changes in leaf color. Also, the measurement is integrated over a larger area and is much easier to do in real time. It can, for example, be done from a tractor or center pivot using one of several rapid, non-destructive methods or from aircraft or satellites using crop reflectance.

Various rapid, non-destructive techniques for assessing standing crop biomass and other related canopy physical attributes such as leaf area index and percent ground cover have also been developed. Included among these is the measurement of canopy reflectance in the visible, near-infrared (NIR), and scattering in microwave regions of the electromagnetic spectrum. Other techniques for rapid, non-destructive estimation of crop standing biomass have included measurements of canopy electrical capacitance, attenuation of β.-particles and other ionizing radiation, and measurements of crop canopy transmittance in certain regions of the solar spectrum (between 300 nm and 3000 nm).

SUMMARY

In accordance with one embodiment, a method of determining a nitrogen requirement for vegetation in a field is disclosed. The method includes continuously measuring spectral reflectance received at a measuring device positioned proximate to the field. The measuring device includes a spectrometer measuring light in two or more wavelengths. Based on the measured reflectance, a nitrogen level of a plant canopy of the field is determined. Based on the measured reflectance, a biomass of the plant canopy of the field is determined. Based on the determined nitrogen level of the plant canopy and the biomass of the plant canopy, a nitrogen requirement of the vegetation is determined.

In accordance with another embodiment, a system is provided includes a measuring device having a spectrometer configured to measure two or more wavelengths of shortwave radiation and a control unit electrically coupled to the spectrometer. The control unit is configured to continuously measure spectral reflectance received at the measuring device positioned proximate to the field. The measuring device comprises a spectrometer measuring light in two or more wavelengths. The control unit is further configured to, based on the measured reflectance, determine a nitrogen level of a plant canopy of vegetation planted in the field. The control unit is further configured to, based on the measured reflectance, determine a biomass of the plant canopy of vegetation planted in the field. The control unit is further configured to, based on the determined nitrogen level of the plant canopy and the biomass of the plant canopy, determine a nitrogen requirement of the vegetation planted in the field.

BRIEF DESCRIPTION OF THE DRAWINGS

It is believed that certain embodiments will be better understood from the following description taken in conjunction with the accompanying drawings, in which like references indicate similar elements and in which.

DETAILED DESCRIPTION

Figure 1:
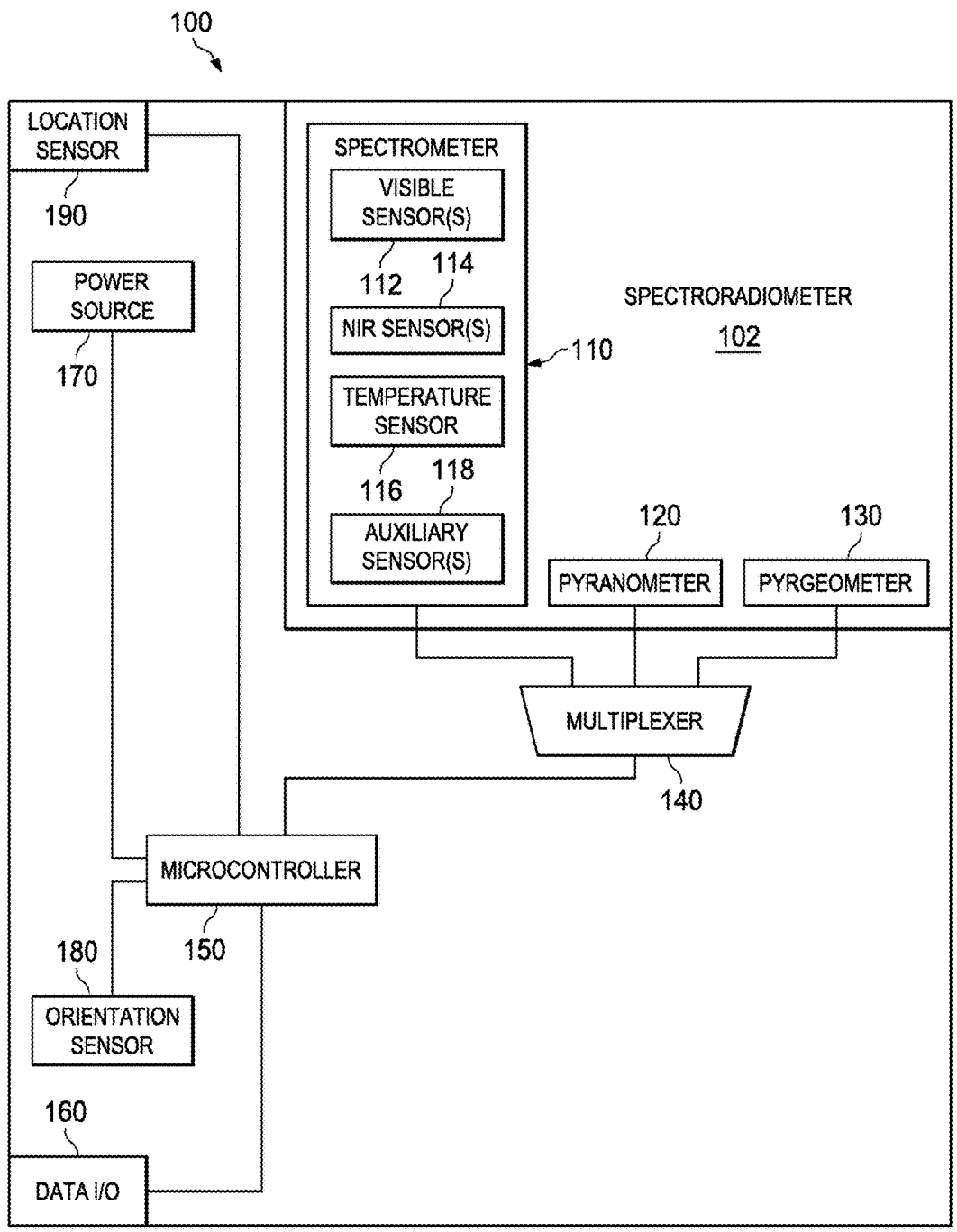
FIG. 1 depicts a simplified block diagram of an example radiation measuring device in accordance with one non-limiting embodiment.
Figure 2:
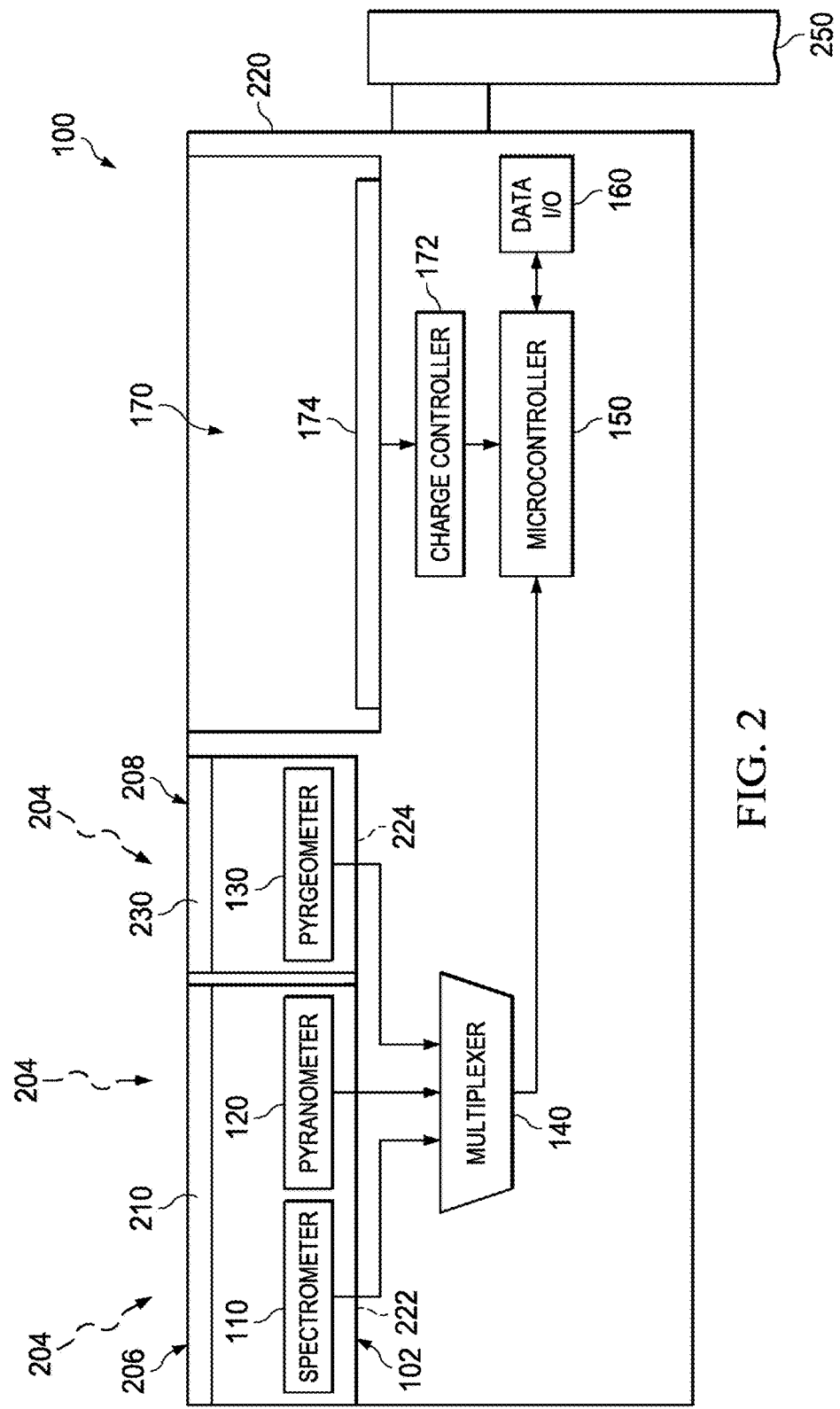
FIG. 2 is a side schematic block diagram of the radiation measuring device shown in FIG. 1.
Figure 3:
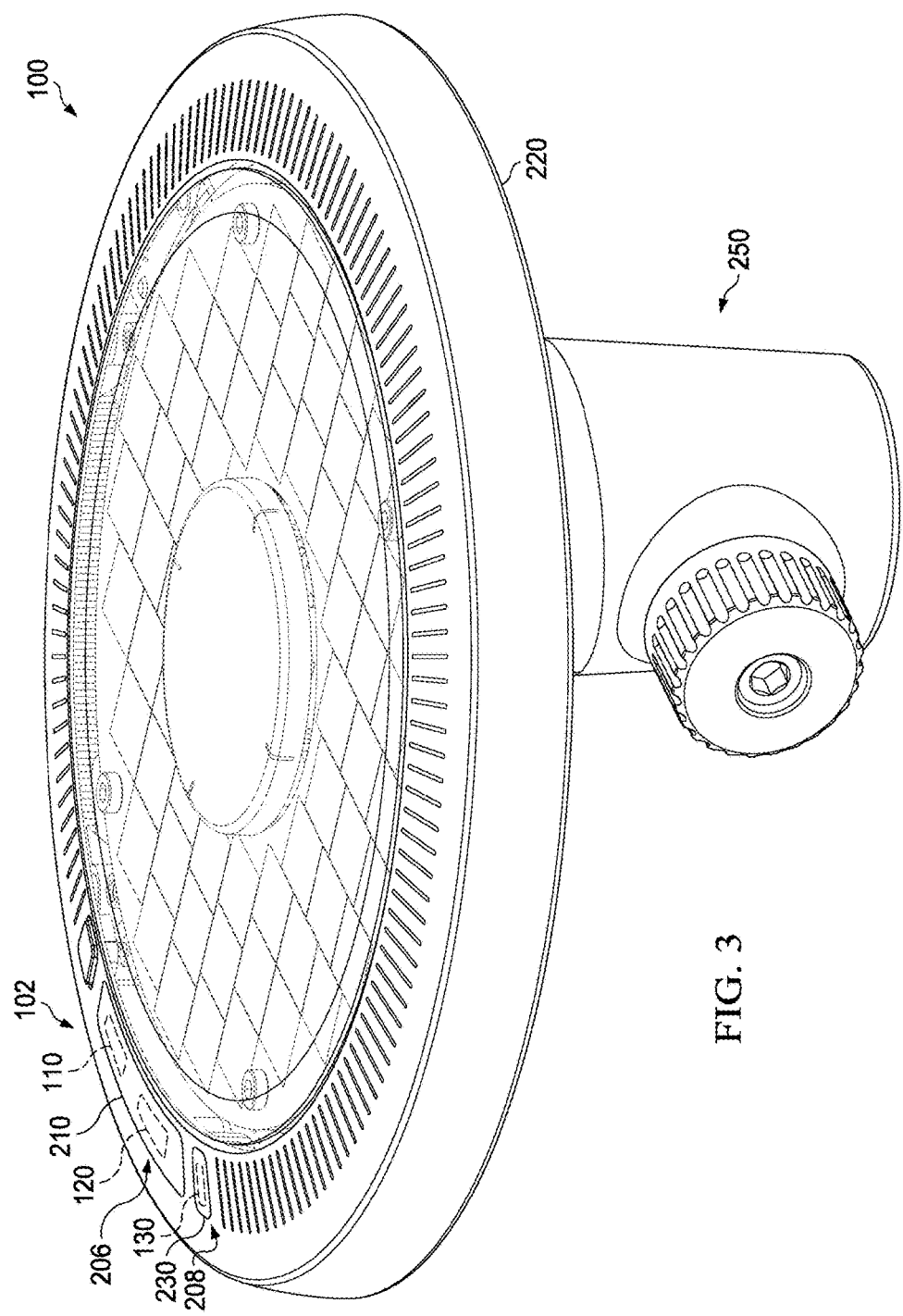
FIG. 3 is an isometric view of the example radiation measuring device depicted in FIG. 1.
Figure 4:
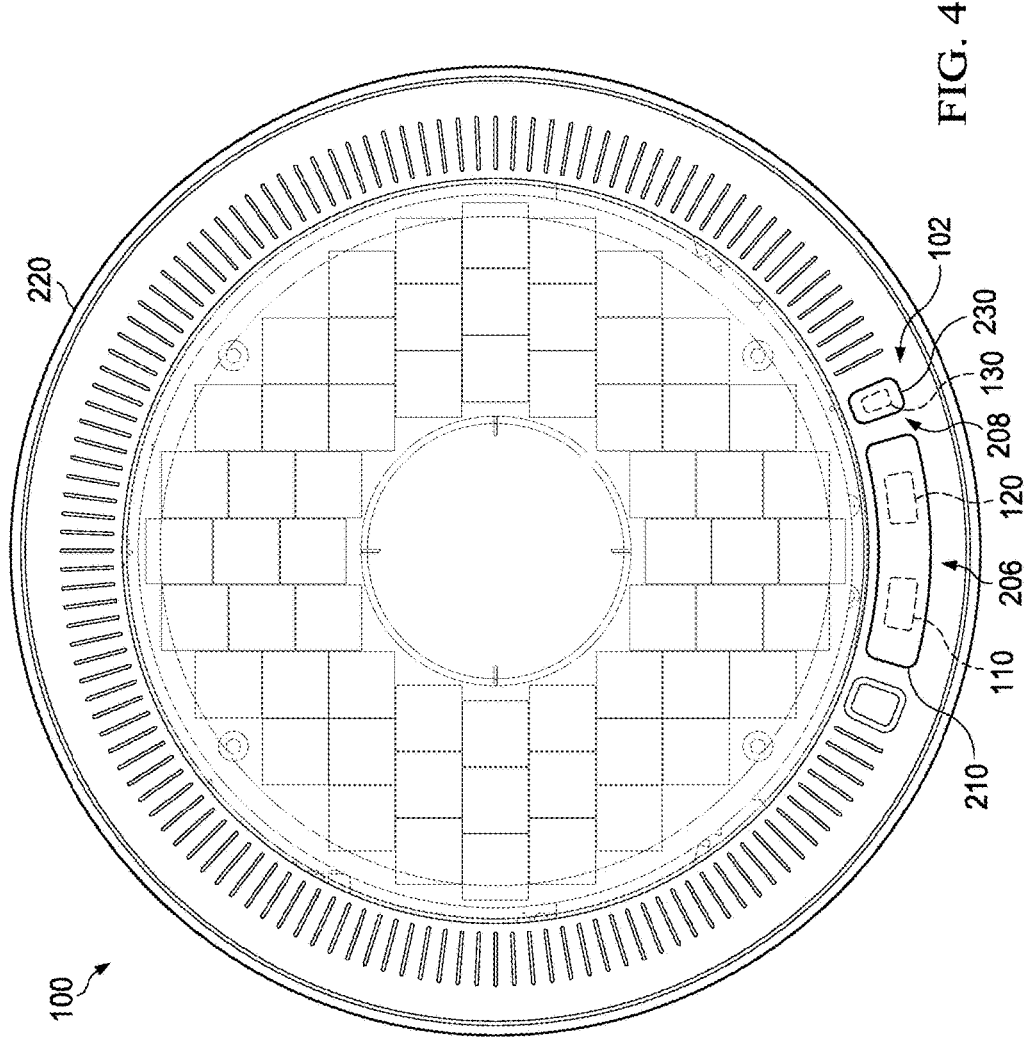
FIG. 4 is a top plan view of the example radiation measuring device shown and depicted in FIGS. 1 and 3.
Figure 5:
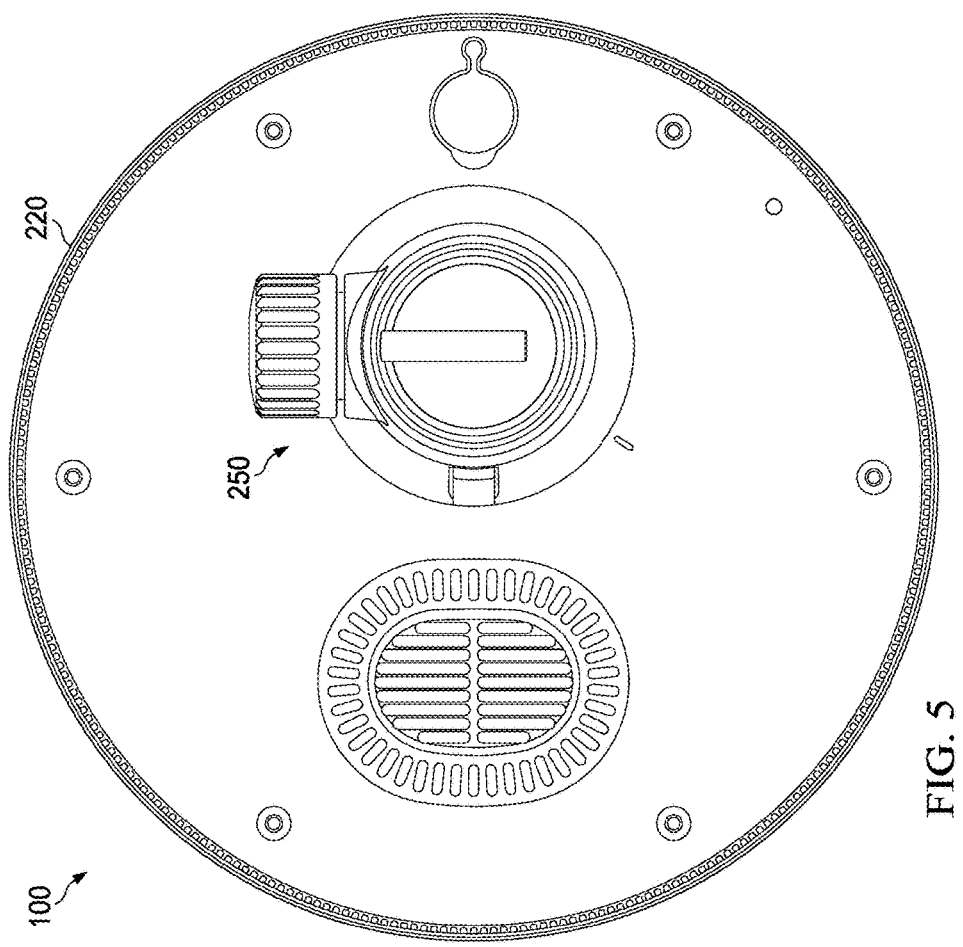
FIG. 5 is a bottom plan view of the example radiation measuring device shown and depicted in FIGS. 1 and 3.
Figure 6:
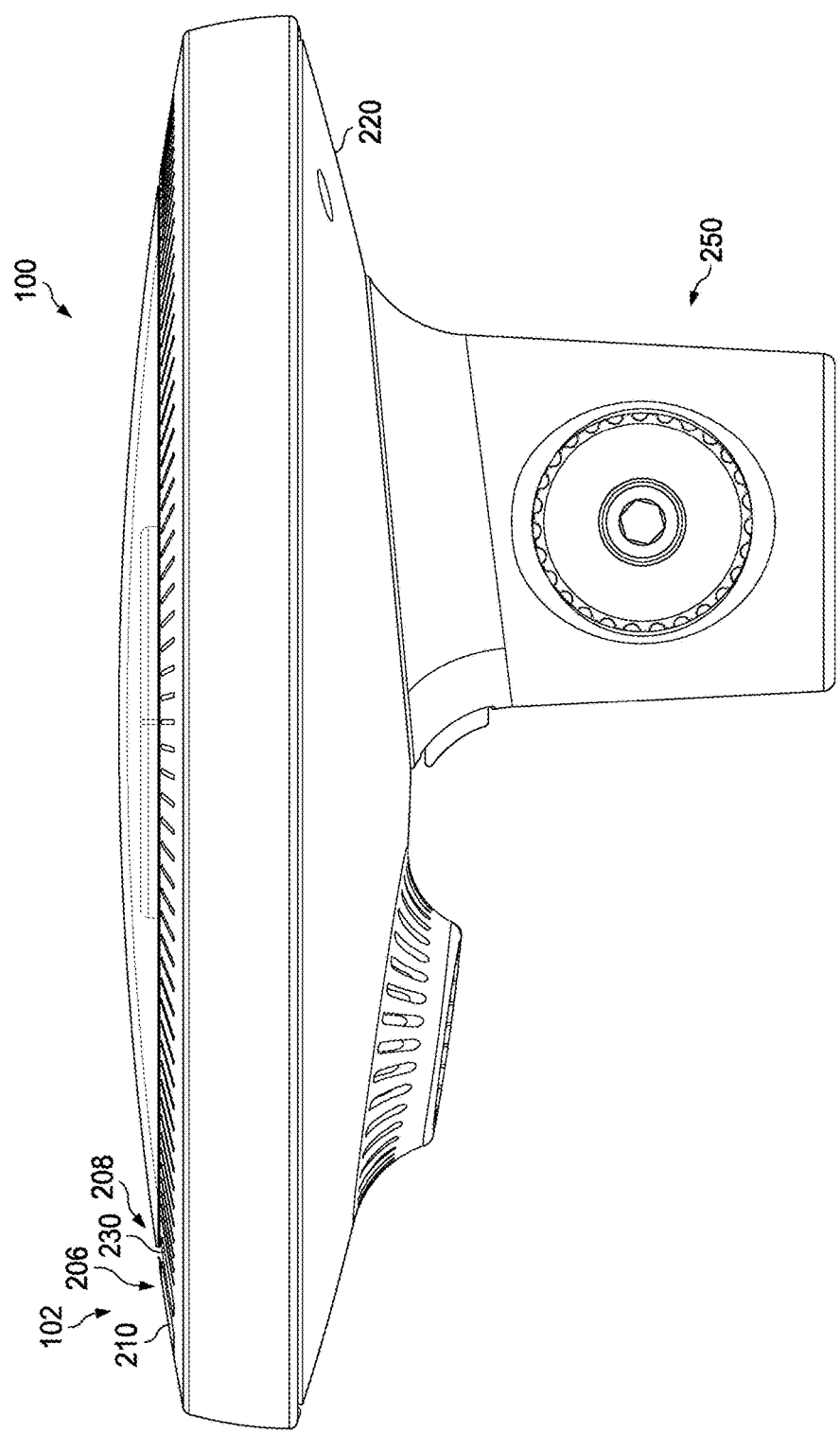
FIG. 6 is a front elevation view of the example radiation measuring device shown and depicted in FIGS. 1 and 3.
Figure 7:
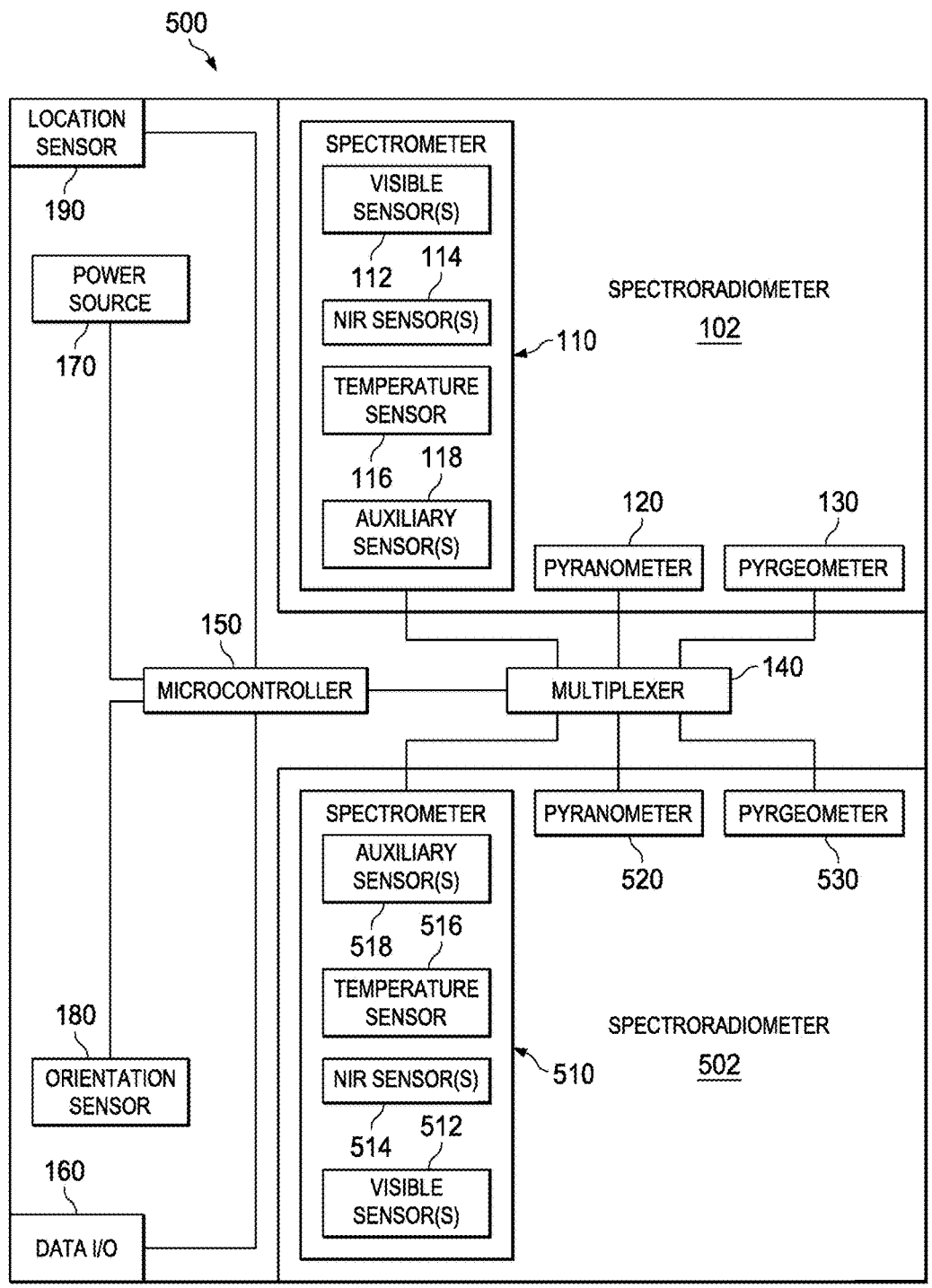
FIG. 7 depicts a simplified block diagram of another example radiation measuring device in accordance with one non-limiting embodiment.
Figure 8:
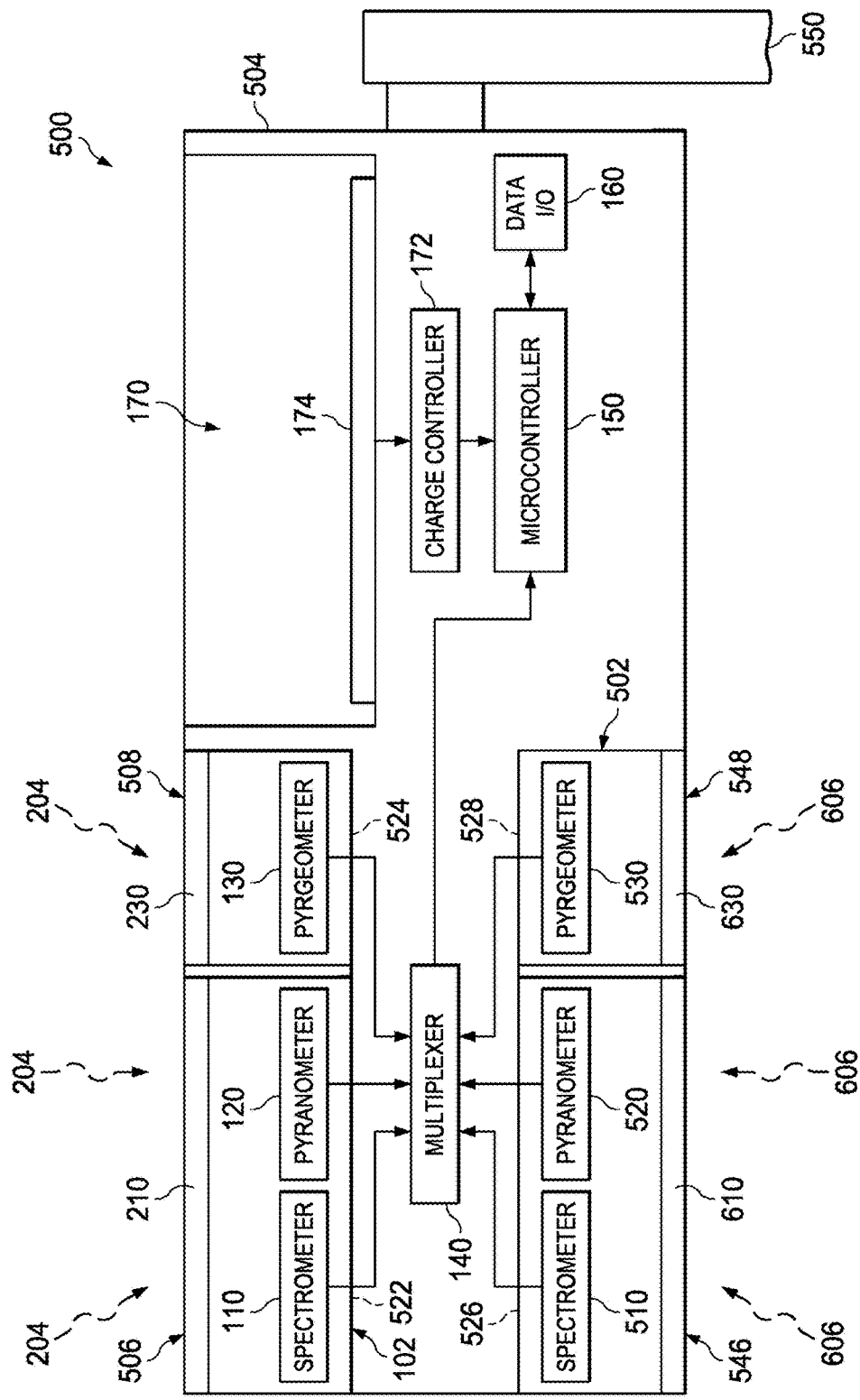
FIG. 8 is a side schematic block diagram of the radiation measuring device shown in FIG. 7.
Figure 9:
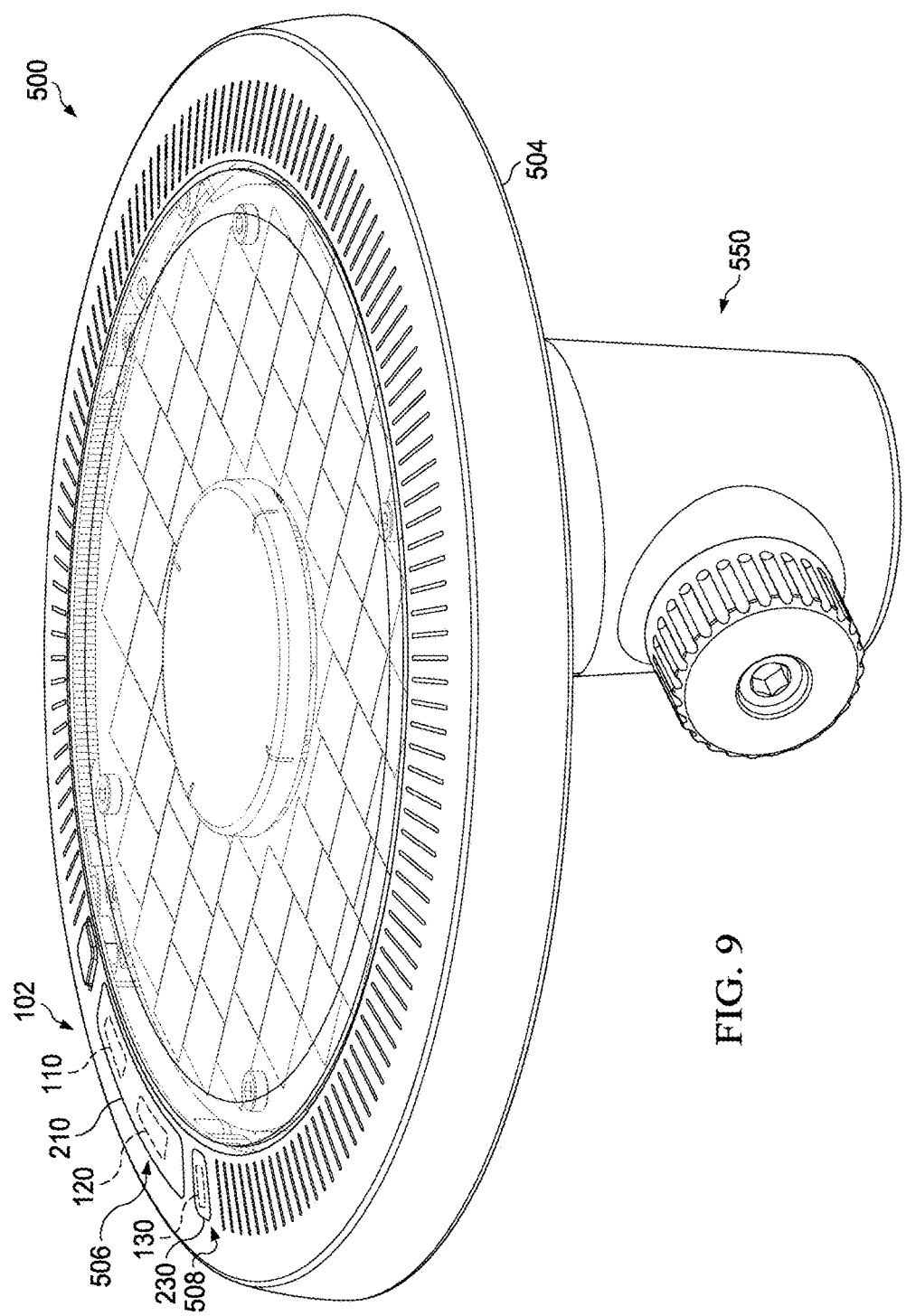
FIG. 9 is an isometric view of the example radiation measuring device depicted in FIG. 7.
Figure 10:
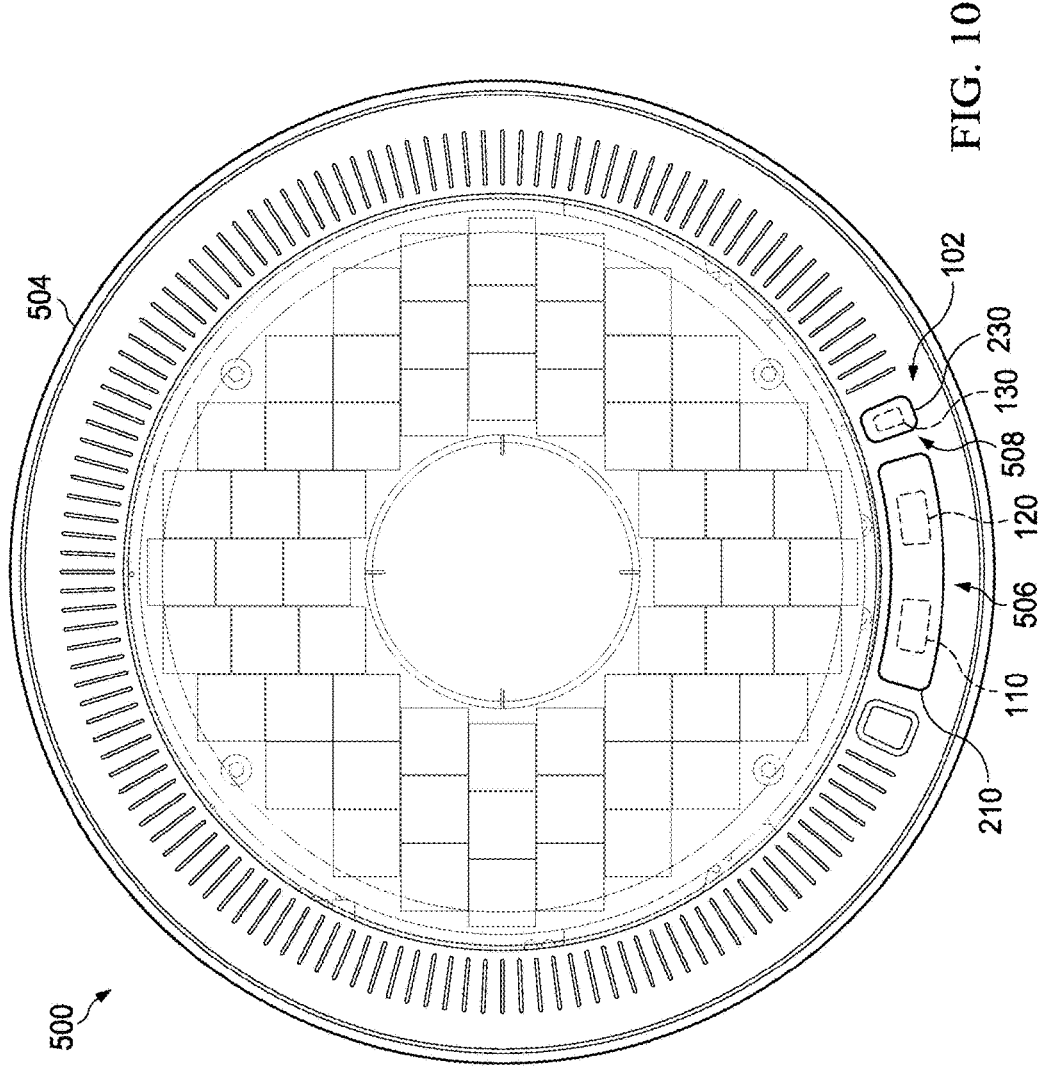
FIG. 10 is a top plan view of the example radiation measuring device shown and depicted in FIGS. 7 and 9.
Figure 11:
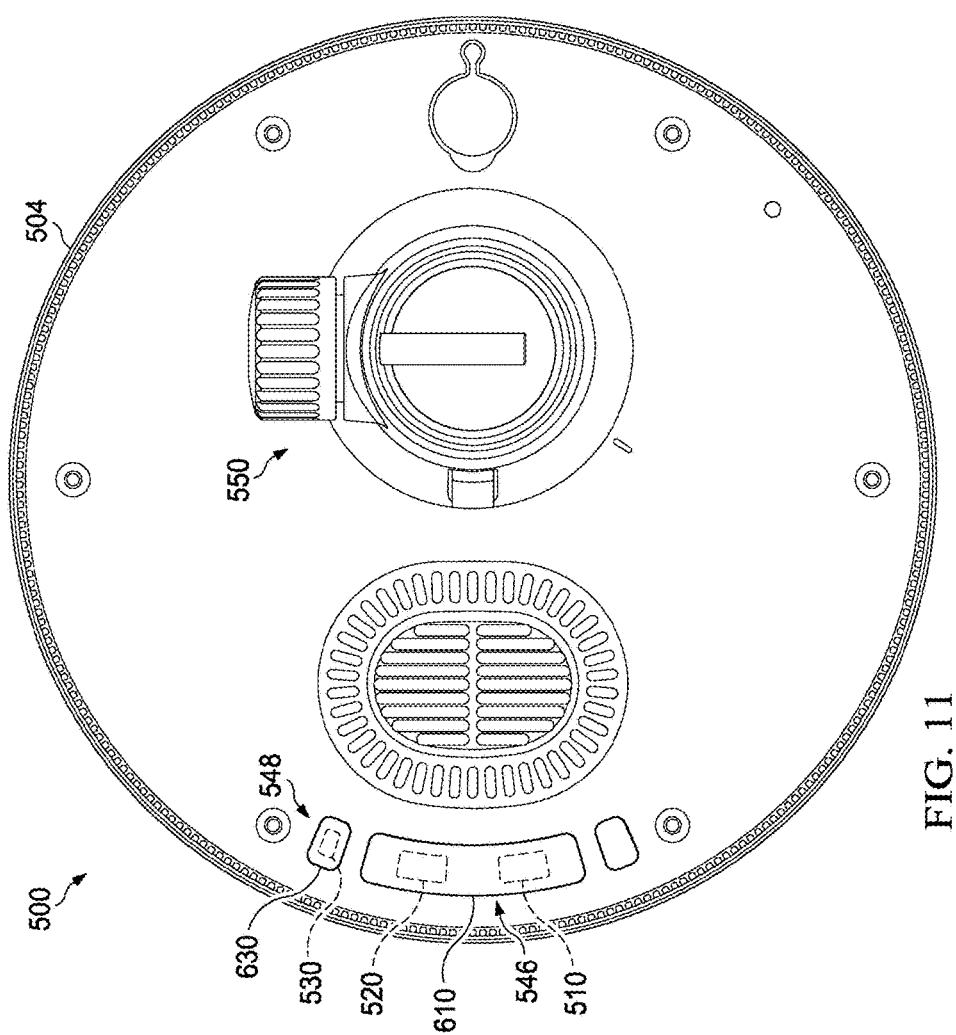
FIG. 11 is a bottom plan view of the example radiation measuring device shown and depicted in FIGS. 7 and 9.
Figure 12:
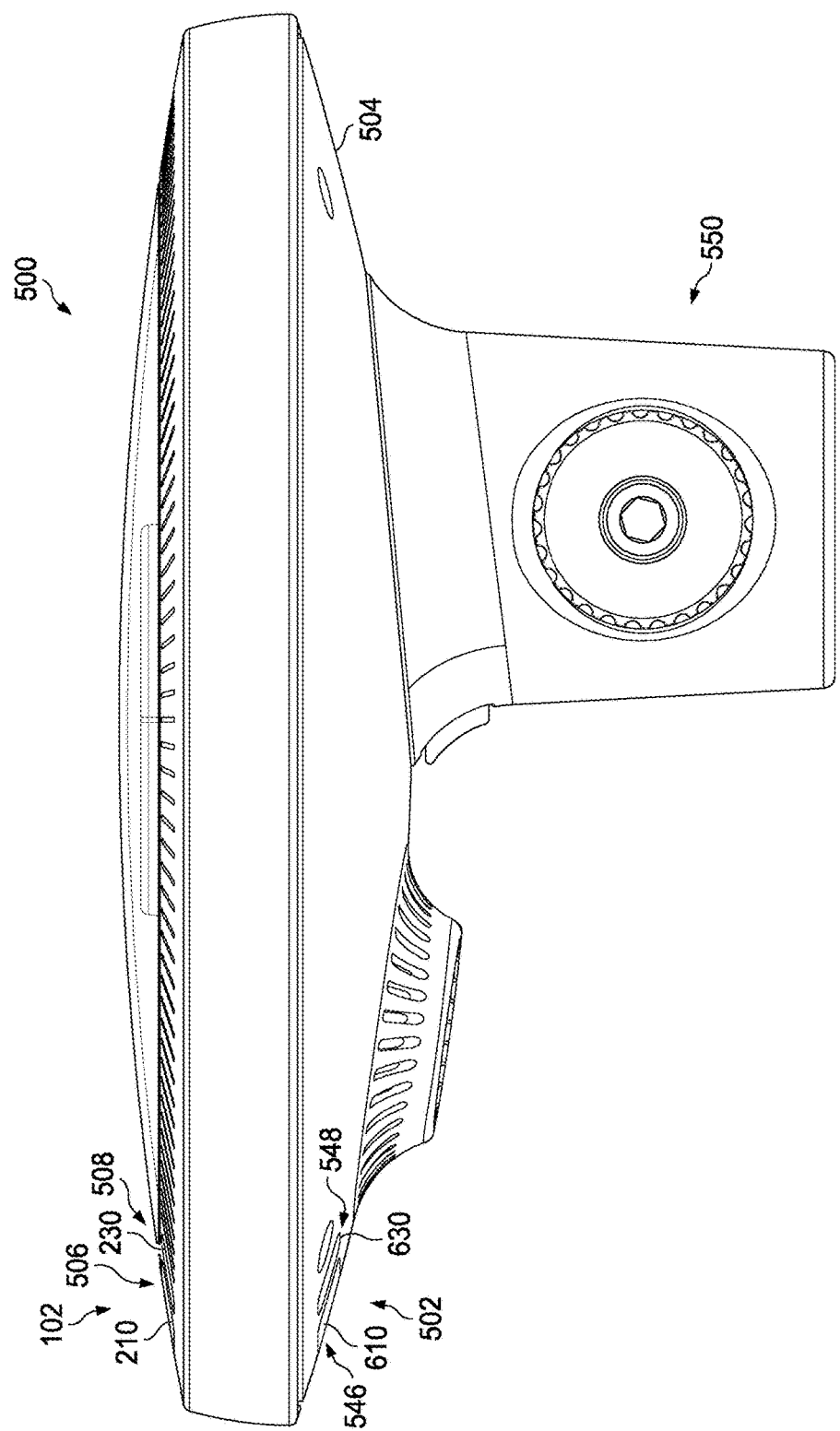
FIG. 12 is a front elevation view of the example radiation measuring device shown and depicted in FIGS. 7 and 9.

Various non-limiting embodiments of the present disclosure will now be described to provide an overall understanding of the principles of the structure, function, and use of the apparatuses, systems, methods, and processes disclosed herein. One or more examples of these non-limiting embodiments are illustrated in the accompanying drawings. Those of ordinary skill in the art will understand that systems and methods specifically described herein and illustrated in the accompanying drawings are non-limiting embodiments. The features illustrated or described in connection with one non-limiting embodiment may be combined with the features of other non-limiting embodiments. Such modifications and variations are intended to be included within the scope of the present disclosure.

Reference throughout the specification to "various embodiments", "some embodiments", "one embodiment", "some example embodiments", "one example embodiment", or "an embodiment" means that a particular feature, structure, or characteristic described in connection with any embodiment is included in at least one embodiment. Thus, appearances of the phrases "in various embodiments", "in some embodiments", "in one embodiment", "some example embodiments", "one example embodiment", or "in an embodiment" in places throughout the specification are not necessarily all referring to the same embodiment. Furthermore, the particular features, structures or characteristics may be combined in any suitable manner in one or more embodiments.

For the purposes of radiometry, the radiation budget at a point can said to be composed of radiation originating from the sun, termed shortwave radiation, and radiation originating from the organic and inorganic components of the Earth system, termed longwave radiation. A detector for shortwave radiation is termed a pyranometer, whereas a detector for longwave radiation is termed a pyrgeometer. Shortwave radiation is largely confined to wavelengths from 300-3000 nm and includes light that is perceptible to humans (visible light or VIS) as well as light at higher frequencies (ultraviolet or UV) and lower frequencies (near infrared or "NIR"). This shortwave radiation might come directly from the sun, without interaction with other materials before reaching a detector, in which case it is known as the direct component shortwave radiation. Alternatively, this shortwave radiation might scattered by atmospheric constituents (gases, aerosols, clouds) before reaching a detector indirectly. Scattered light coming from the sky is known as the diffuse component of radiation. Finally, some fraction of light reaching materials on Earth could be reflected from the surface before reaching the detector. While in principle reflected light could come from above or below the detector, often the detector is positioned such that downwelling radiation is composed largely of direct and diffuse components of solar radiation, and upwelling radiation is composed largely of reflected light from materials on the Earth's surface. Longwave infrared radiation as defined here is confined to wavelengths from 8000-15,000 nm, and is emitted by all matter, proportionally to its temperature and its chemical composition, which determines its emissivity.

For the purposes of shortwave spectroscopy, the Earth's surface can broadly be said to be comprised of soil, photosynthetic vegetation ("PV"), such as leaves, and non-photosynthetic vegetation ("NPV"), such as wood, bark, dead leaves, and so forth. PV possesses a variety of pigments that reflect (r), transmit (t) and absorb (b) light in a wavelength-dependent fashion. Chief among these pigments are chlorophyll, carotenoids, and anthocyanin. The absorption of these pigments in certain spectral regions is so strong as to render the leaf nearly optically black with even small amounts of these pigments present. Such is the case of the absorption of chlorophyll in the blue and red regions. Where there is weaker absorption, such as in the green region, there is slightly greater reflectance. This slight difference in reflectance is what makes a healthy leaf appear green.

By contrast, the lack of absorption of these pigments in other regions, particularly the near infrared (700 nm<λ<2400 nm), renders leaves optically bright, with incident sunlight about evenly split between reflection and transmission. This sharp difference in absorption in the visible and near infrared (NIR) is known as the red edge, and is used as a diagnostic of biological activity. The existence of this red edge exists in contrast to the absorption spectrum of soils, water, or non-photosynthetic vegetation, which is relatively flat.

The contrast in reflectance from the red region to the NIR region, owing to the presence of PV overlying soil, led to the development of "vegetation indices" that can be used to infer leaf area from airborne or satellite measurements of reflectance. For example, the "Normalized Difference Vegetation Index" (NDVI) can be calculated as follows:

$$NDVI = \frac{\rho_{nir} - \rho_{vis}}{\rho_{nir} + \rho_{vis}}$$

A tight relationship exists between the "Normalized Difference Vegetation Index" (NDVI) and the leaf area index (LAI; m²leaf), as presented in Sellers, P. J. (1985). Canopy reflectance, photosynthesis and transpiration. International Journal of Remote Sensing, 6(8), 1335-1372. It should be appreciated that the total canopy absorption follows Beer's law, which can be express as follows:

$$I(LAI) = I_0 * e^{(-kLAI)}$$

Since the total canopy absorption follows Beer's law, the total canopy absorption of photosynthetically active radiation is closely tied to NDVI as well. Thus, NDVI is a proxy for total absorption of light by the leaf canopy, which itself is in part a determinant of total productivity. In accordance with the present disclosure, conventional NDVI can be measured as follows:

$$NDVI = \frac{NIR - R}{NIR + R}$$

One shortcoming to the use of NDVI is its saturation above LAI~3.5. However, Gitelson et al. (1996) proposed that a Green NDVI (GNDVI) would have wider dynamic range. [Gitelson, A. A., Kaufman, Y. J., & Merzlyak, M. N. (1996). Use of a green channel in remote sensing of global vegetation from EOS-MODIS. *Remote Sensing of Environment*, 58(3), 289-298.] GNDVI can be calculated by the following:

$$GNDVI = \frac{NIR - G}{NIR + G}$$

In the red band, leaves show high absorption at even low levels of chlorophyll, so the sensitive variable is the NIR. By contrast, a Green NDVI has weaker absorption in the green, so as there is greater LAI, the green band lowers, and the NIR band increases. This has the effect of expanding the dynamic range of the index, while also being sensitive to chlorophyll concentration. Gitelson et al (1996) also proposed a Green "Atmospherically Resistant" Index (GARI) that would be less impacted by aerosols, which are diagnosed by contrasts in reflectance between the blue and the red. Aerosols absorb in the blue band, which is why smog/haze has a reddish tint. The GARI can be calculated by the following:

$$GARI = \frac{NIR - [G - \lambda(B - R)]}{NIR + [G - \lambda(B - R)]}$$

The GARI is echoed by the "Enhanced Vegetation Index" (EVI) proposed by Gitelson et al. (2008) [Gitelson, A. A., Vina, A., Masek, J. G., Verma, S. B., & Suyker, A. E. (2008). Synoptic Monitoring of Gross Primary Productivity of Maize Using Landsat Data. *IEEE Geoscience and Remote Sensing Letters*, 5(2), 133-137.] The EVI can be calculated by the following:

$$EVI = \frac{2.5(NIR - R)}{1 + NIR + 6R - 7B}$$

$$WDRVI = \frac{\alpha NIR - R}{\alpha NIR + R}$$

The strong absorption by chlorophyll in some regions, particularly the blue and red, renders reflectance measurements in these regions unsuitable for use in inferring chlorophyll concentration. The strong specific absorption of chlorophyll is such that small quantities of chlorophyll cause total leaf absorption to saturate at low concentrations, while the range of biological interest is orders of magnitude wider. Thus, the ideal places to measure reflectance for determination of chlorophyll concentration are those regions where chlorophyll absorbs slightly. This ensures that chlorophyll has some absorption, so that the reflectance changes when more pigment is present, but not so much that the response saturates quickly. This is found in regions around λ=550 nm and λ=725 nm as confirmed by S. L. Ustin et al. (2009) [Ustin, S. L., Gitelson, A. A., Jacquemoud, S., Schaepman, M., Asner, G. P., Gamon, J. A., & Zarco-Tejada, P. (2009). Retrieval of foliar information about plant pigment systems from high resolution spectroscopy. *Remote Sensing of Environment*, 113, S67-S77.]

Spectrometers are instruments used for measuring wavelengths of light spectra in accordance with the above. Spectrometers may be used to measure the properties of light for a variety of applications including environmental or chemical analysis, fluorescence, or Raman spectroscopy. Spectrometers are optical instruments that can detect spectral lines and measure their wavelength or intensity. Spectrometers are ideal for determining compositional makeup of a surface by means of analysis of the spectrum of reflected light. Spectrometers can also be used to determine the composition of a material or gas by analyzing the measured spectrum in reference to a known spectrum of a light source passing through the material or gas. Spectrometers can also be used to test the efficiency of an optical filter in order to determine whether a filter has properly blocked or transmitted specific wavelengths. Spectrometers can also be used to improve the performance of pyranometers or pyrgeometers by providing estimates of phenomena that can introduce noise or error into the signal, for example water vapor in the atmosphere that could impact the longwave emissivity of the sky, or spectral correction of incident light onto a photodiode.

An issue with spectrometers is that they measure the raw energy coming from a source (also known as the radiance), whereas the relevant measure to interpret is the reflectance, namely the ratio of radiation from the source to the incident radiation. Spectrometer systems in accordance with the present disclosure beneficially measure the actual reflectance, using twinned light sensors measuring incident and reflected radiation in each of several spectral bands.

Another issue with many spectrometers is the sensitivity to the specific geometry of illumination and observation. Imaging spectrometers in particular (e.g., from satellites, aircraft, or unmanned aerial vehicles) observe a very small solid angle in each pixel, and the decontamination of so-called "bidirectional" effects is central to the quality assurance and quality control procedures for these images. By contrast, spectrometer systems in accordance with the present disclosure have a diffuser on top and bottom which integrates incident light across the entire hemisphere (upper or lower) thereby removing, or at least reducing, the presence of view-angle effects. This configuration allows for a measure of the true reflectance of the surface, rather than the "bidirectional reflectance factor" that is measured with a directional spectrometer.

Pyranometers can broadly be divided into two categories: those that use a thermoelectric effect to measure incident shortwave radiation by use of thermopiles, and those that use a photoelectric effect by use of photodiodes. In general, instruments relying on the thermoelectric effect are considered more accurate, and are more expensive. While photodiodes have an advantage due to their low cost and simplicity of design, they suffer from two shortcomings: they have a limited range of spectral sensitivity, generally between 400-1100 nm, and within that range, they vary in their sensitivity to light of different wavelengths. These two phenomena mean that the performance of photoelectric pyranometers is limited to settings where the incoming radiation has the same spectral quality as the light where the instrument was calibrated. Thus, photoelectric pyranometers can have large errors when measuring upwelling shortwave radiation generally, or measuring downwelling radiation in the morning and evening (when blue from the sky is more prevalent than red from the sun), or measuring downwelling radiation under smoke, haze, or other aerosol contamination. These errors are such that corrections using an accompanying spectrometer can improve performance of photoelectric pyranometers.

Another issue with pyranometers is degradation of performance as diffusers situated above the detector degrade from exposure to UV light or chemicals, or are covered with contaminants such as dust or pollen. The errors introduced by these phenomena may also be diagnosed by an accompanying spectrometer, which can detect slow and persistent changes in the spectral quality of received radiation.

Pyrgeometers generally employ a thermoelectric effect using a thermopile to measure thermal radiation emitted from a target. One issue with pyrgeometers is the interpretation of the power of the received radiation as the temperature of the target, using the Stefan-Boltzmann relation, for example:

$$LW = \varepsilon \sigma T_K^4$$

where $\varepsilon$ is the emissivity of the target, $\sigma$ is the Stefan-Boltzmann constant (i.e., $5.67 \times 10^{-8}$), and $T_K$ is the temperature of the target in Kelvin.

Generally, errors originate in the need to assume an emissivity of 1.0 for arbitrary targets of unknown composition. For example, the emissivity of vegetation and soil for upwelling can be close to 1, whereas the emissivity of the sky is closer to 0.75. Furthermore, the emissivity of the sky is dependent on its water vapor content. Because water vapor has a higher emissivity, the bulk emissivity of an atmosphere with greater water vapor is larger. In the absence of this additional information, the inversion of the Stefan-Boltzmann equation to retrieve the target temperature is prone to error.

FIGS. 1-6 depict simplified block diagrams various views of an example radiation measuring device 100 in accordance with one non-limiting embodiment. The radiation measuring device 100 includes a spectroradiometer 102 configured to sense and/or measure amounts of electromagnetic radiation 204 originating from one or more sources external to the radiation measuring device 100. For example, in the illustrative embodiment, the spectroradiometer 102 is configured to sense and/or measure amounts of visible shortwave radiation, near-infrared (NIR) shortwave radiation, and longwave radiation that originate from the sun (i.e., solar radiation) and/or that are reflected by other objects. To do so, the spectroradiometer 102 includes a spectrometer 110, a pyranometer 120, and a pyrgeometer 130. In some embodiments, the spectroradiometer 102 and/or each of the spectrometer 110, the pyranometer 120, and the pyrgeometer 130 are in electrical communication with a multiplexer 140, which may in turn be in electrical communication with a microcontroller 150 (e.g., a control unit). In other embodiments (not shown), the spectroradiometer 102 and/or each of the spectrometer 110, the pyranometer 120, and the pyrgeometer 130 are in direct electrical communication with the microcontroller 150. It should be appreciated that, in some embodiments, the microcontroller 150 may include the multiplexer 140.

The spectrometer 110 may include one or more sensors or components configured to sense radiation and/or other environmental conditions. For example, as illustratively shown in FIG. 1, the spectrometer 110 may include one or more visible electromagnetic radiation sensors 112 (e.g., visible light sensors), one or more near-infrared (NIR) electromagnetic radiation sensors 114, one or more temperature sensors 116, and/or one or more auxiliary sensors 118. The one or more visible electromagnetic radiation sensors 112 are configured to sense and/or measure the amount of visible shortwave radiation originating from source(s) external to the radiation measuring device 100. Additionally, the one or more NIR electromagnetic radiation sensors 114 are configured to sense and/or measure the amount of NIR shortwave radiation originating from source(s) external to the radiation measuring device 100. For example, the visible electromagnetic radiation sensor(s) 112 and the NIR electromagnetic radiation sensor(s) 114 may be configured to sense and/or measure amounts of visible and NIR shortwave radiation that originate from the sun (i.e., solar radiation) and/or that are reflected by other objects. In some embodiments, one or more of the sensors of the spectrometer 110 are configured to measure radiation within a water absorption band (i.e., radiation having a wavelength centered at about 950 nm or about 1450 nm).

The pyranometer 120 of the spectroradiometer 102 may include one or more sensors also configured to sense and/or measure the amount of shortwave radiation originating from source(s) external to the radiation measuring device 100. In some embodiments, the pyranometer 120 is configured to sense and/or measure the amount of visible shortwave radiation originating from source(s) external to the radiation measuring device 100. Additionally, or alternatively, the pyranometer 120 is configured to sense and/or measure the amount of NIR shortwave radiation originating from source(s) external to the radiation measuring device 100. The pyrgeometer 130 of the spectroradiometer 102 is configured to sense and/or measure the amount of longwave radiation originating from source(s) external to the radiation measuring device 100.

The radiation measuring device 100 can also include a data input/output (I/O) module 160. The data I/O module 160 can include communication circuitry such as, for example, one or more wireless communication radios or modules to support various wireless communication protocols (e.g., Wifi-based protocols, LTE or GSM protocols, BLUETOOTH protocols, near field communication protocols, satellite protocols, cellular protocols, etc.). In some embodiments, the data I/O module 160 can also provide for wired interfaces, such as a USB interface, an Ethernet interface, and so forth. In some operational environments, the radiation measuring device 100 can generally function as a weather monitor to enable various data-intensive natural resource management or civil infrastructure management software services. The data I/O module 160 can be used by the radiation measuring device 100 to transmit data (e.g., radiation measurement data, location data, orientation data, sensor data, diagnostic data, health data, etc.) to a data collection server or a radiation analysis device in real-time, substantially real-time, or in batch format. Additionally, or alternatively, the data I/O module 160 can be used by the radiation measuring device 100 to receive data from one or more sensors (not shown), such as sensors for measuring soil moisture, air quality, water pressure and flow, electrical current, and so forth. Additional tools, such as soil moisture and salinity monitoring devices, a camera, or equipment monitors can be interface with one or more ports of the data I/O module 160.

The radiation measuring device 100 also includes a power source 170. The power source 170 is configured to generate power to satisfy some or all of the power consumption requirements of the radiation measuring device 100. For example, in the illustrative embodiment, the power source 170 includes a solar array 174 configured to be exposed to sunlight for generation of power for the radiation measuring device 100. The solar array 174 may be in electrical communication with a charge controller 172 which can include, for example, a maximum power point controller or voltage regulator. In some embodiments, onboard power storage sources can be utilized (i.e., solar-charged battery cells, etc.) to store and supply power to the radiation measuring device 100.

In some embodiments, the radiation measuring device 100 may also include an orientation sensor 180 configured to determine a levelness of the radiation measuring device 100 and/or components or portions thereof. For example, the orientation sensor 180 may be configured to determine whether one or more sensor areas are level relative to a reference plane. In some embodiments, the orientation sensor 180 is embodied as a bubble level, a magnetometer, and/or any other device or combinations of devices configured to operate as a tilt sensor or level. Furthermore, the radiation measuring device 100 can include a location sensor 190 (e.g., a Global Positioning System (GPS) sensor, RF triangulation circuitry, a compass, etc.) for generating location data or other geospatial data indicative of the physical location of the radiation measuring device 100. In accordance with various embodiments, the pyranometer 120 and the location sensor 190, such as a GPS, are used to estimate solar angle and fraction of actual to potential radiation. Such factors can be used, for example, to correct the estimates of reflectance for illumination conditions, as described below.

The microcontroller 150 (e.g., control unit, processor, etc.) is in communication (e.g., via direct or indirect electrical communication) to the various components of the radiation measuring device 100. In the illustrative embodiment, the microcontroller 150 receives measurements and/or data generated by the spectrometer 110, the pyranometer 120, the pyrgeometer 130, the data I/O module 160, the orientation sensor 180, the location sensor 190, and/or any other component of the radiation measuring device 100. For example, in some embodiments, the microcontroller 150 receives one or more voltages generated by each of sensors (e.g., the spectrometer 110, the pyranometer 120, the pyrgeometer 130, etc.) indicative of the amount of shortwave and/or longwave electromagnetic radiation measured. It should be appreciated that, in some embodiments, the measurements and/or data generated the spectrometer 110, the pyranometer 120, the pyrgeometer 130, and/or any other components of the spectroradiometer 102 may be first received by the multiplexer 140 and then transmitted to the microcontroller 150 for further processing.

In some embodiments, the radiation measuring device 100 may include a mounting assembly 250 (FIGS. 2, 3, 5, and 6). In such embodiments, the mounting assembly 250 may be configured to facilitate mounting the radiation measuring device 100 to a post. It should be appreciated that while the mounting assembly 250 is shown to facilitate mounting the radiation measuring device 100 to a post, other mounting assemblies can be used.

The radiation measuring device 100 includes one or more diffusers configured to scatter electromagnetic radiation received from external source(s). For example, as depicted in FIGS. 2-4 and 6, the radiation measuring device 100 includes a diffuser 210 (e.g., a first diffuser) configured to cover the spectrometer 110 and the pyranometer 120. The diffuser 210 may be embodied as or otherwise include one or more thermoplastic materials. For example, in some embodiments, the diffuser 210 includes a polycarbonate material or an acrylic material. In such embodiments, the diffuser 210 is configured to scatter visible electromagnetic shortwave radiation and near-infrared electromagnetic shortwave radiation received from external source(s) prior to being sensed and/or measured by the spectrometer 110 and the pyranometer 120.

Additionally, in some embodiments, the radiation measuring device 100 also includes a separate diffuser 230 (e.g., a second diffuser) configured to cover the pyrgeometer 130. The diffuser 230 may be embodied as or otherwise include one or more thermoplastic materials different from the diffuser 210. For example, in some embodiments, the diffuser 230 includes a polyethylene material. In such embodiments, the diffuser 230 is configured to scatter electromagnetic radiation received from external source(s) prior to being sensed and/or measured by the pyrgeometer 130.

As depicted in FIGS. 2-6, the radiation measuring device 100 has a housing 220 that includes various the various components described herein. For example, as illustratively shown, the spectrometer 110 and the pyranometer 120 are positioned in a sensor zone (e.g., a first sensor zone 206) of the radiation measuring device 100. Additionally, the pyrgeometer 130 is positioned in separate sensor zone (e.g., a second sensor zone 208) of the radiation measuring device 100, which may or may not be adjacent to the first sensor zone 206. In such embodiments, the spectrometer 110 may be configured to measure visible shortwave radiation received at the first sensor zone 206. Furthermore, the pyranometer 120 may be configured to measure visible shortwave radiation and, in some embodiments, near-infrared shortwave radiation, received at the first sensor zone 206. The pyrgeometer 130 may be configured to measure longwave radiation received at the second sensor zone 208. In this arrangement, the diffuser 210 and the diffuser 230 may be positioned to cover the first sensor zone 206 and the second sensor zone 208, respectively.

In some embodiments, the housing 220 of the radiation measuring device 100 may define a recess or cavity for each sensor zone. For example, the housing may define a recess (e.g., a first recess 222) at the first sensor zone 206 within which the spectrometer 110 and the pyranometer 120 are positioned. The housing 220 may also define another recess (e.g., a second recess 224) at the second sensor zone 208 within which the pyrgeometer 130 is positioned. In such an arrangement, the diffuser 210 may be configured to cover the first recess 222 thereby covering the spectrometer 110 and the pyranometer 120. Additionally, the diffuser 230 may be configured to cover the second recess 224 thereby covering the pyrgeometer 130.

Referring now to FIGS. 7-12, an example radiation measuring device 500 in accordance with another non-limiting embodiment is shown. The radiation measuring device 500 includes the spectroradiometer 102 (i.e., the spectrometer 110, the pyranometer 120, the pyrgeometer 130, and other components), the microcontroller 150 (e.g., control unit), the data I/O module 160, and the power source 170 of the radiation measuring device 100 shown in FIGS. 1-6 and described herein. In some embodiments, the radiation measuring device 500 may also include the multiplexer 140, the orientation sensor 180, and the location sensor 190 of the radiation measuring device 100 shown in FIGS. 1-6 and described herein. It should be appreciated that such components of the radiation measuring device 500 may be configured substantially similar to, and perform functionality substantially similar to, the components of the radiation measuring device 100, as described herein.

The radiation measuring device 500 also includes a second spectroradiometer 502 also configured to sense and/or measure amounts of visible shortwave radiation, near-infrared (NIR) shortwave radiation, and longwave radiation that originate from the sun (i.e., solar radiation) and/or that are reflected by other objects. To do so, the spectroradiometer 502 includes a spectrometer 510, a pyranometer 520, and a pyrgeometer 530. In some embodiments, the spectroradiometer 502 and/or each of the spectrometer 510, the pyranometer 520, and the pyrgeometer 530 are in electrical communication with the multiplexer 140, which as discussed herein, may be in electrical communication with the microcontroller 150 (e.g., the control unit). In other embodiments (not shown), the spectroradiometer 502 and/or each of the spectrometer 510, the pyranometer 520, and the pyrgeometer 530 are in direct electrical communication with the microcontroller 150.

Similar to the spectrometer 110, the spectrometer 510 may include one or more sensors or components configured to sense radiation and/or other environmental conditions. For example, as illustratively shown in FIG. 7, the spectrometer 510 may include one or more visible electromagnetic radiation sensors 512 (e.g., visible light sensors), one or more near-infrared (NIR) electromagnetic radiation sensors 514, one or more temperature sensors 516, and/or one or more auxiliary sensors 518. It should be appreciated that such components of the radiation measuring device 500 may be configured substantially similar to, and perform functionality substantially similar to, the visible electromagnetic radiation sensor(s) 112, the NIR electromagnetic radiation sensor(s) 114, temperature sensor(s) 116, and/or auxiliary sensor(s) 118 of the spectrometer 110 of the radiation measuring device 100, described herein. In some embodiments, one or more of the sensors of the spectrometer 510 are configured to measure radiation within a water absorption band (i.e., radiation having a wavelength centered at about 950 nm or about 1450 nm).

In some embodiments, the radiation measuring device 500 may include a mounting assembly 550 (FIGS. 8, 9, 10, and 12). In such embodiments, the mounting assembly 550 may be configured to facilitate mounting the radiation measuring device 500 to a post. It should be appreciated that while the mounting assembly 550 is shown to facilitate mounting the radiation measuring device 500 to a post, other mounting assemblies can be used.

Similar to the radiation measuring device 100, the radiation measuring device 500 includes one or more diffusers configured to scatter electromagnetic radiation received from external source(s). For example, as depicted in FIGS. 8-12, the radiation measuring device 500 includes the diffuser 210 configured to cover the spectrometer 110 and the pyranometer 120. The radiation measuring device 500 includes a separate diffuser 230 configured to cover the pyrgeometer 130. Additionally, as shown, the radiation measuring device 500 includes the diffuser 610 and the diffuser 630. The diffuser 610 is configured to cover the spectrometer 510 and the pyranometer 520. In some embodiments, the diffuser 610 may be embodied as or otherwise include one or more thermoplastic materials such as, for example, a polycarbonate material or an acrylic material. The diffuser 630 is configured to cover the pyrgeometer 530 and may be embodied as or otherwise include one or more thermoplastic materials different from the diffuser 610. For example, in some embodiments, the diffuser 630 includes a polyethylene material.

As depicted in FIGS. 9-12, the radiation measuring device 500 has a housing 504 that includes various the various components described herein. For example, as illustratively shown, the spectrometer 110 and the pyranometer 120 are positioned in a sensor zone (e.g., a first sensor zone 506) of the radiation measuring device 500. The pyrgeometer 130 is positioned in separate sensor zone (e.g., a second sensor zone 508) of the radiation measuring device 500. Additionally, the spectrometer 510 and the pyranometer 520 are positioned in another sensor zone (e.g., a third sensor zone 546) of the radiation measuring device 500, and the pyrgeometer 530 is positioned in yet another sensor zone (e.g., a fourth sensor zone 548) of the radiation measuring device 500. In this arrangement, the diffuser 210 and the diffuser 230 may be positioned to cover the first sensor zone 506 and the second sensor zone 508, respectively. Additionally, the diffuser 610 and the diffuser 630 may be positioned to cover the third sensor zone 546 and the fourth sensor zone 548, respectively.

As shown, the first and second sensor zones 506, 508 may be oriented in one direction (e.g., a first direction) relative to the housing 504 of the radiation measuring device 500. Additionally, the third and fourth sensor zones 546, 548 may be oriented in another direction (e.g., a second direction) relative to the housing 504 of the radiation measuring device 500. In the illustrative embodiment shown, the orientation direction of the third and fourth sensor zones 546, 548 is substantially opposite the orientation direction of the first and second sensor zones 506, 508. For example, as shown, the first and second sensor zones 506, 508 can be positioned on a first side (e.g., a top side) of the housing 504 of the radiation measuring device 500 and oriented in one direction whereas the third and fourth sensor zones 546, 548 can be positioned on a second side (e.g., a bottom side) of the housing 504 of the radiation measuring device 500 and oriented in a direction opposite to the direction in which the first and second sensor zones 506, 508 are oriented.

In such arrangements, the spectrometer 110, the pyranometer 120, and the pyrgeometer 130 or, more generally, the spectroradiometer 102, is configured to measure shortwave and longwave downwelling electromagnetic radiation originating from source(s) external to the radiation measuring device 500 (e.g., solar radiation, etc.) and received at the first and second sensor zones 506, 508. For example, the spectrometer 110 may be configured to measure visible shortwave radiation and near-infrared shortwave radiation received at the first sensor zone 506. The pyranometer 120 may be configured to measure visible shortwave radiation and, in some embodiments, near-infrared shortwave radiation, received at the first sensor zone 506. Additionally, the pyrgeometer 130 may be configured to measure longwave radiation received at the second sensor zone 508.

Furthermore, the spectrometer 510, the pyranometer 520, and the pyrgeometer 530 or, more generally, the spectroradiometer 502, is configured to measure shortwave and longwave upwelling electromagnetic radiation originating from source(s) external to the radiation measuring device 500 (e.g., reflected radiation, etc.). For example, the spectrometer 510 may be configured to measure visible shortwave radiation and near-infrared shortwave radiation received at the third sensor zone 546. The pyranometer 520 may be configured to measure visible shortwave radiation and, in some embodiments, near-infrared shortwave radiation, received at the third sensor zone 546. Additionally, the pyrgeometer 530 may be configured to measure longwave radiation received at the fourth sensor zone 548.

In some embodiments, the housing 504 of the radiation measuring device 500 may define a recess or cavity for each sensor zone. For example, the housing 504 may define a recess (e.g., a first recess 522) at the first sensor zone 506 within which the spectrometer 110 and the pyranometer 120 are positioned. The housing 504 may also define another recess (e.g., a second recess 524) at the second sensor zone 508 within which the pyrgeometer 130 is positioned. The housing 504 may define a further recess (e.g., a third recess 526) at the third sensor zone 546 within which the spectrometer 510 and the pyranometer 520 are positioned. The housing 504 may also define another recess (e.g., a fourth recess 528) at the fourth sensor zone 548 within which the pyrgeometer 530 is positioned. In such an arrangement, the diffuser 210 may be configured to cover the first recess 522 thereby covering the spectrometer 110 and the pyranometer 120. Additionally, the diffuser 230 may be configured to cover the second recess 524 thereby covering the pyrgeometer 130. The diffuser 610 may be configured to cover the third recess 526 thereby covering the spectrometer 510 and the pyranometer 520. Furthermore, the diffuser 630 may be configured to cover the fourth recess 528 thereby covering the pyrgeometer 530.

It should be appreciated that by having an upward pointing spectroradiometer (i.e., the upper spectroradiometer 102), atmospheric pollutants can be measured using the attenuation of downwelling light (i.e., radiation) in certain wavelengths in reference to an uncontaminated spectrum. Further, by having a downward pointing spectroradiometer (i.e., the lower spectroradiometer 502), the accuracy of the sensors over a wider array of light conditions can be improved, which is useful in applications for measuring and analyzing upwelling radiation. Upwelling radiation has a very different spectrum than downwelling radiation, so the errors could be large if calibrations for the downwelling radiation were to be applied to the upwelling radiometer. By having downward pointing spectroradiometer (i.e., the lower spectroradiometer 502), vegetation cover and composition can be measured.

Further, devices for measuring plant reflectance conventionally only measure a pair of wavelengths, (e.g., the red and NIR for NDVI, or the red edge and NIR for Chlorophyll, or the 530/570 pair for PRI). The radiation measuring devices 100, 500 of the present disclosure, however, combine a number of spectral bands, allowing for a complete set of measurements of characterize the plant. Consider the following model of plant photosynthesis:

$$GPP = eps * fAPAR * PAR$$

where GPP is gross primary productivity, eps is light use efficiency, PAR is photosynthetically active radiation, and fAPAR is the fraction of absorbed PAR. (Gitelson, IEEE 2008).

In accordance with the present disclosure, photosynthetically active radiation (PAR) may be directly measured using a silicon photodiode. Absorbed PAR (APAR) may be determined as follows:

$$APAR = (1 - \text{ratio of upelling to downwelling PAR})$$

The factor f is measured as the fraction of absorbed PAR (fAPAR) by means of a NDVI. Finally, eps is measured using the photochemical reflectance index (PRI) and chlorophyll concentration. Moreover, unlike conventional practice which measures the vegetation state occasionally, the light environment may be measured continuously (or at least at a relatively high sample frequency), allowing estimates of gross primary productivity (GPP) to be integrated over time.

The light use efficiency (LUE) is impacted by stresses that reduce the efficiency of chlorophyll to turn light energy into chemical energy. The radiation measuring device 500 may measure or monitor other phenomena indicative of heat and water stresses that are the common mechanisms for reduced light use efficiency. The radiation measuring device 500 may also measure leaf temperature using a non-contact thermopile (e.g., the pyrgeometer 530), as well as air temperature, and the leaf-to-air-temperature difference becomes a measure of heat stress. The radiation measuring device 500 may also measure absorption of water in the leaf using reflectance in the ~950 and ~1450 nm regions, as a measure of leaf relative water content, which is correlated to leaf water potential. Leaf water potential can be used for evaluating leaf water stress, for example.

Moreover, a spectrometry challenge to separating direct and diffuse constituents of shortwave radiation amounts to knowing the position of the sun in relation to a location on Earth, and from this knowledge calculating how much sunlight should be received in a clear atmosphere. The radiation measuring devices 100, 500 disclosed herein may decipher, or facilitate the determination of, whether dimness is due to clouds (which have a flat impact on the radiation) or due to aerosols (which have a selective impact on certain wavelengths), or due to the path length of the sun through the atmosphere (Mie scattering). Because the radiation measuring devices 100, 500 may have a variety of onboard sensors, such as the location sensor 190 and the orientation sensor 180, the solar position in relation to the upper spectroradiometer 102 and the lower spectroradiometer 502 can be determined. In doing so, the radiation measuring devices 100, 500 may be configured to determine or facilitate the determination of the air mass, which can be used to determine an estimate of Mie scattering. Accordingly, three different causes of light diffusion may be measured or considered, which provides an estimate of diffuse fraction.

In some embodiments, the radiation measuring devices 100, 500 are configured to communicate with a radiation analysis device (not shown). It should be appreciated that the radiation analysis device can be embodied as any type of computing device or server capable of performing the functions described herein. For example, the radiation analysis device can be embodied as a microcomputer, a minicomputer, a custom chip, an embedded processing device, a mobile computing device, a laptop computer, a handheld computer, a smart phone, a tablet computer, a personal digital assistant, a telephony device, a desktop computer, a mainframe, or other computing device and/or suitable programmable device capable of processing, communicating, storing, maintaining, and transferring data. As such, the radiation analysis device can include devices and structures commonly found in computing devices such as processors, memory devices, communication circuitry, and data storages, which are not shown in the figures for clarity of the description. It should be appreciated that, in some embodiments, the radiation analysis device can include one or more processors (e.g., CPUs, processing units, etc.) that execute instructions stored on a computer-readable or machine-readable medium to perform one or more of the functions described herein. Additionally, or alternatively, the radiation analysis device can include hardware logic (e.g., logic circuits, etc.), software logic, or any combination thereof capable of performing one or more of the functions described herein. As such, in some embodiments, the radiation analysis device may be a special-purpose computing or processing device configured to receive, analyze, or otherwise process measurement data received from the radiation measuring devices 100, 500.

In some embodiments, the radiation analysis device is configured to receive the measurement data (e.g., voltages, values, etc.) generated by each of the spectrometer 110, the pyranometer 120, the pyrgeometer 130, the spectrometer 510, the pyranometer 520, the pyrgeometer 530, and/or any other sensors or devices of the radiation measuring device 500. In such embodiments, the radiation analysis device may be configured to determine an amount of downwelling radiation received at the first sensor zone 506 and the second sensor zone 508 based on the received measurement data. The radiation analysis device may also be configured to determine an amount of upwelling radiation received at the third sensor zone 546 and the fourth sensor zone 548 based on the received measurement data. In some embodiments, the radiation analysis device is configured to determine a ratio of hemispherical upwelling radiation to hemispherical downwelling radiation in at least one spectral band based at least in part on the determined amount of the upwelling radiation and the determined amount of the downwelling radiation. To do so, in some embodiments, one or more sensors of the radiation measuring device 500 may be configured to measure radiation in one or more spectral bands such as, for example, a blue spectral band, a green spectral band, a yellow spectral band, a red spectral band, a red edge spectral band, and a near-infrared spectral band.

Additionally, or alternatively, in some embodiments, the radiation analysis device may be configured to retrieve one or more reference measurement correction factors from a data store (local or remote). In such embodiments, each of the one or more reference measurement correction factors corresponds to a different one of the spectrometer 110, the pyranometer 120, the pyrgeometer 130, the spectrometer 510, the pyranometer 520, the pyrgeometer 530, and/or another sensor or device of the radiation measuring device 500. Based on the reference measurement correction factors, the radiation analysis device may be configured to correct (e.g., adjust, revise, etc.) the corresponding measurement data received from the radiation measuring device 500. For example, the radiation analysis device may be configured to utilize a reference measurement correction factor corresponding to the spectrometer 110 to correct measurement data generated by the spectrometer 110. It should be appreciated that the radiation analysis device can be configured to utilize the corrected measurement data values to determine the amounts of upwelling and downwelling radiation.

As discussed herein, the radiation measuring device 500, in some embodiments, includes a location sensor 190 (e.g., a Global Positioning System (GPS) sensor, RF triangulation circuitry, a compass, etc.) for generating location data or other geospatial data indicative of the physical location of the radiation measuring device 500. In such embodiments, the radiation analysis device may be configured to receive location data from the radiation measuring device 500 indicative of the physical location of the radiation measuring device 500. Based on the received location data, the radiation analysis device can be configured to determine a solar position relative to the physical location of the radiation measuring device 500. Thereafter, the radiation analysis device may be configured to determine an amount of direct radiation and an amount of diffuse radiation based at least in part on a measured amount of solar radiation and a potential amount of solar radiation. The measured amount of solar radiation can be based at least in part on, or otherwise a function of, the determined amount of upwelling radiation and the determined amount of downwelling radiation.

In some embodiments, the radiation analysis device is configured to determine one or more indices from the measurement data received from the radiation measuring device 500. For example, in some embodiments, the radiation analysis device is configured to determine a Photochemical Reflectance Index (PRI) from the received measurement data. Additionally, or alternatively, the radiation analysis device is configured to determine a Normalized Difference Vegetation Index (NDVI) from the received measurement data. The radiation analysis device may also be configured to determine a Chlorophyll Index (CI) from the received measurement data. It should be appreciated that the radiation analysis device may also be configured to determine and/or generate indices that combine one or more of the PRI, NDVI, and CI. In embodiments, in which the radiation analysis device determines a PRI, one or more of the spectrometer 110, the pyranometer 120, the spectrometer 510, and the pyranometer 520 of the radiation measuring device 500 may be configured to measure radiation comprising wavelengths centered at about 530 nm and about 570 nm. In embodiments, in which the radiation analysis device determines a NDVI, one or more of the spectrometer 110, the pyranometer 120, the spectrometer 510, and the pyranometer 520 of the radiation measuring device 500 may be configured to measure radiation comprising wavelengths centered at about 650 nm and about 850 nm. Additionally, in embodiments in which the radiation analysis device determines a CI, one or more of the spectrometer 110, the pyranometer 120, the spectrometer 510, and the pyranometer 520 of the radiation measuring device 500 may be configured to measure radiation comprising wavelengths centered at about 725 nm and about 850 nm.

Figure 13:
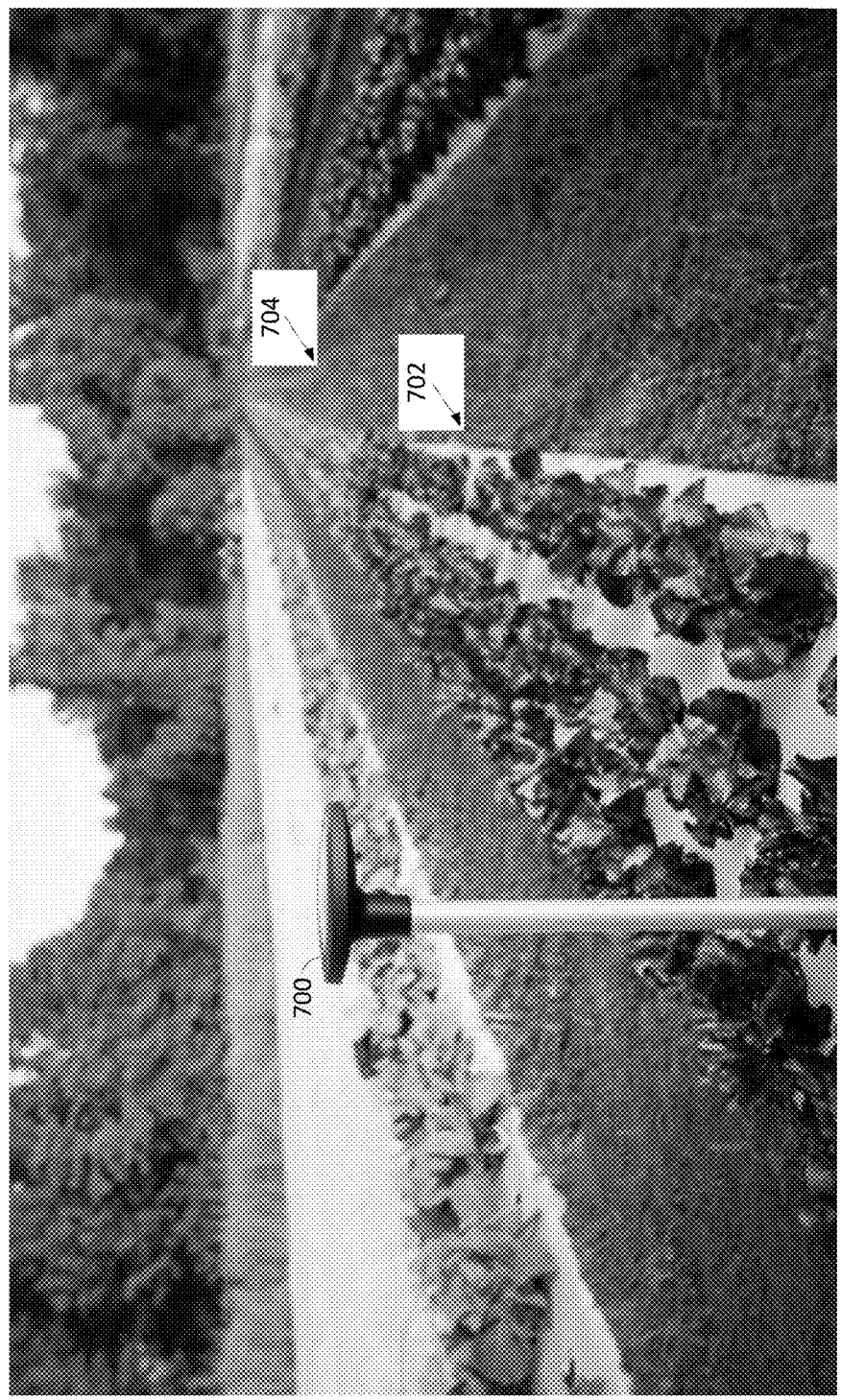
FIG. 13 shows an example radiation measuring device positioned proximate to example crops.

Referring now to FIG. 13, an example radiation measuring device 700 is shown positioned proximate to example crops 702 planted in a field 704. In accordance with various embodiments, the radiation measuring device 700 can be similar to either radiation measuring device 100 or radiation measuring device 500, described above. As is to be appreciated, the type and amount of crops 702, size of the filed 704, etc., can vary. Further, in some embodiments, the radiation measuring device 700 can further include an acoustic disdrometer, as described in U.S. Pat. No. 9,841,533, issued on Dec. 12, 2017, entitled DISDROMETER HAVING ACOUSTIC TRANSDUCER AND METHODS THEREOF, the disclosure of which is incorporated herein by reference in its entirety.

Determining parameters associated with the application of fertilizer to the crops 702 is challenged by inadequate constraints on key factors that determine how much fertilizer to apply, and when to apply the fertilizer. As described herein, the systems and methods in accordance with the present embodiments make use of prior information (e.g. from field trials), time series data, and episodic but spatially extensive satellite data, to constrain these uncertainties.

Constraining the Amount of Nitrogen (N) To Be Applied

Referring first to techniques for constraining the amount of nitrogen (N) to be applied, let there be a field 704 in which seeds for the crops 702 have been planted (at t=0), and seeds have begun to grow such that leaves are present, and all biomass is either leaf or root, with no biomass in reproductive tissue (i.e. grain). A determination of the amount of additional N to apply at time t in order to meet a yield goal for harvest (t=T) is desired. The mass balance equation for the additional N requirement, assuming no losses, immobilization or soil drawdown, is:

$$N_{requirement,t} = N_T - N_{canopy,t}$$

Where $N_T$ is defined as the whole-plant N requirement. The yield goal (kg C/m$^2$) can be defined by expert opinion, a numerical model, or a statistical expectation from prior outcomes, and is treated here as an exogenous variable. This yield goal is converted to N units via the C:N ratio of the seeds ($CN_{seed}$), normalized to a whole plant level by the nitrogen harvest index ($HI_N$), both determined from literature values or prior phenotyping:

$$N_T = \text{Yield Goal} \times CN_{seed}^{-1} \times HI_N^{-1}$$

$$HI_N = \frac{\text{kg } N_{seed}}{\text{kg } N_{AGB}}$$

$$CN_{seed} = \frac{\text{kg } C_{seed}}{\text{kg } N_{seed}}$$

It can be shown that if the C or N in above ground biomass (AGB) is the sum of each constituent in the seed and canopy (kg $N_{AGB}$=kg $N_{seed}$+kg $N_{canopy}$) and the harvest index HI=kg $C_{seed}$/kg $C_{AGB}$, then $$HI_N = \frac{CN_{seed} \times \text{Yield Goal}}{CN_{canopy} \times \text{Yield Goal} \times \left(\frac{1-HI}{HI}\right) + CN_{seed} \times \text{Yield Goal}}$$

Since $N_T$ is likely determined before the seed is cast, the unknown parameter is the N already present in the canopy at time t, $N_{canopy,\,t}$. This value can be determined from the radiation measuring device 700, by way of its ability to measure the chlorophyll absorption in the plant canopy, knowing that canopy N concentration is highly correlated with leaf chlorophyll concentration. In accordance with the presently disclosed framework, canopy N is further broken down into chemical and structural components:

$$N_{canopy} = N_{leaf} * SLA * LAI = N_{leaf} * C_{canopy}$$

Where $$N_{leaf} = \frac{\text{kg } N_{leaf}}{\text{kg } C_{leaf}},$$

$$SLA = \frac{\text{kg } C_{leaf}}{m_{leaf}^2}, \text{ and}$$

$$LAI = \frac{m_{leaf}^2}{m_{ground}^2}$$

The product of the specific leaf area (SLA) and the leaf area index (LAI) is the canopy biomass, $C_{canopy}$ (kg C/m$^2$). For the purposes of this work SLA can be considered a constant for a crop species or variety, just as CN and HI values.

Because the radiation measuring device 700 measures spectral indices that separately characterize the nitrogen content of the canopy, as well as the biomass of the canopy, $N_{canopy}$ can be estimated by spectral reflectance using various vegetation indices:

$$C_{canopy} = f_1(\rho_M)$$

$$N_{leaf} = f_2(\rho_M)$$

Where $\rho_M$ is an array of reflectances (including bands such as the red and near infrared used for NDVI, the red edge used in a chlorophyll index), and the subscript M refers to these being collected by the radiation measuring device 700, at coordinates ($x_M$, $y_M$). The functions relating these spectral reflectances to physical units are $f_1$ and $f_2$ respectively, and can include one of the many functional forms proposed (SVI, NDVI, EVI, WDRVI, MSAVI, CI), as well as the regression coefficients necessary to convert the index into units of $N_{canopy}$, $N_{leaf}$ or $C_{canopy}$. One complication to this separation of $N_{canopy}$ into $N_{leaf}$ and $C_{canopy}$ is that the vegetation indices that are used to measure N content sense absorption in the entire canopy, and thus $N_{leaf}$ must be estimated from $N_{canopy}$ and $C_{canopy}$:

$$N_{canopy,M} = f_3(\rho_M)$$

$$N_{leaf,M} = \frac{f_3(\rho_M)}{f_1(\rho_M)}$$

The relevance for separating out $N_{leaf}$ and $C_{canopy}$ from $N_{canopy}$ is twofold. First, the use of $N_{leaf}$ field and lab chemical assays have led to a wide array of recommendations and diagnostics based on $N_{leaf}$, and an overall intuition behind this measure as a key performance indicator. Second, commodity Earth observing satellites (Landsat, Geoeye, Planet) only measure the spectral reflectances to constrain $C_{canopy}$ but not $N_{canopy}$, or in other words measure NIR reflectance but not red-edge reflectance. The implication of this is in the use of satellite data to estimate $N_{canopy}$ at positions in the field that are not below the radiation measuring device 700 ($x_S,y_S$)≠($x_M,y_M$):

$$C_{canopy,S} = f_1(\rho_S)$$

A problem arises that the reflectances measured by the satellite or other type of airborne collection device are prone to error, owing to, for example, imperfect calibrations of the sensors, oblique viewing geometry of a narrow solid angle of a reflected light, image capture at some date previous to the time of calculation, and atmospheric contamination. A correction factor can be applied to reflection data collected from the airborne collection device. In some embodiments, the correct factor is based on the downwelling light spectrum collected within the scene of the airborne imager in comparison to a clear-sky spectrum to infer atmospheric contamination. Thus, under a simplifying assumption that the satellite error is off by a simple ratio of the true value, a corrected value of $C_{canopy}$ can be estimated as $$C'_{canopy,S} = f_1\left(\rho_S \frac{\rho_M}{\rho_{SM}}\right),$$

where $\rho_{SM}$ is the reflectance of the satellite at the coordinate of the radiation measuring device 700 $(x_{SM}, y_{SM}) = (x_M, y_M)$. This can be simplified by representing the correction term as a gain factor $\beta$:

$$\beta = \frac{\rho_M}{\rho_{SM}}.$$

In summary this leaves the N requirement at any position in the field to be calculated as:

$$N_{requirement,t} = \text{Yield Goal} \times CN_{seed}^{-1} \times HI_N^{-1} - N_{leaf,M} * C_{canopy,S}$$

Constraining the Time at which N Reaches Deficiency

Another framework for making fertilizer recommendations is to identify the time at which $N_{leaf}$ reaches a lower threshold value, which is considered deficient, $N^*_{leaf}$. $N_{leaf}$ can be calculated as before, but with an additional time subscript, t, and dropping the M subscript for simplicity:

$$N_{leaf,t} = \frac{f_3(\rho_t)}{f_1(\rho_t)}$$

Assuming that as the plant grows and leaves expand that $N_{leaf}$ follows first order rate kinetics described by:

$$\frac{dN_{leaf,t}}{dt} = -k \times N_{leaf,t},$$

such that $N_{leaf,t2} = N_{leaf,t1} \cdot \exp(-k(t2-t1))$. Then, k can be estimated from two subsequent observations of $N_{leaf}$.

$$k = -\frac{\ln\left(\frac{N_{leaf,t2}}{N_{leaf,t1}}\right)}{t2-t1},$$

or using noisy data, as the regression of $\ln(N_{leaf})$ and t. From this estimate of k, the time t* at which $N^*_{leaf}$ is reached can be calculated as $$t^* = t_0 - \frac{\ln\left(\frac{N^*_{leaf}}{N_{leaf,t0}}\right)}{k}.$$

Constraining the Efficiency of Fertilizer Uptake

A further uncertainty in the application of fertilizer is the uptake efficiency, or the amount of applied fertilizer that is taken up by the crop, and not lost to leaching, volatilization, denitrification, or immobilization. In accordance with the present disclosure, rates of plant nitrogen uptake from the soil based on sequential measurements can be estimated along with rates of translocation from leaves to other organs, such as grain. Utilizing the estimate of nitrogen translocation, the nitrogen or protein content of the harvested biomass can also be estimated. The fertilizer uptake efficiency (FUE) can be defined as:

$$FUE = \frac{\text{Additional } N \text{ in Crop}}{\text{Additional } N \text{ applied}}$$

This additional N in the crop ($dN_{canopy}$) can be calculated as the simple difference between canopy N estimated at or around the time of application ($t_1$) and some subsequent time (e.g., perhaps a week or two later ($t_2$)):

$$dN_{canopy} = N_{canopy,t2} - N_{canopy,t1}$$

At a point scale, in the footprint of the radiation measuring device 700, this can be calculated as:

$$dN_{canopy} = N_{canopy,M,t2} - N_{canopy,M,t1}$$

However, at a field scale there may be variation in the uptake owing to variations in soils and associated loss factors, leading to a field average value:

$$dN_{canopy} = \frac{\int_A N_{leaf,M,t2} * C_{canopy,S,t2} dA - \int_A N_{leaf,M,t2} * C_{canopy,S,t2} dA}{\int_A dA}$$

The examples discussed herein are examples only and are provided to assist in the explanation of the apparatuses, devices, systems and methods described herein. None of the features or components shown in the drawings or discussed below should be taken as mandatory for any specific implementation of any of these the apparatuses, devices, systems or methods unless specifically designated as mandatory. For ease of reading and clarity, certain components, modules, or methods may be described solely in connection with a specific figure. Any failure to specifically describe a combination or sub-combination of components should not be understood as an indication that any combination or sub-combination is not possible. Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

In general, it will be apparent to one of ordinary skill in the art that at least some of the embodiments described herein can be implemented in many different embodiments of software, firmware, and/or hardware. The software and firmware code can be executed by a processor or any other similar computing device. The software code or specialized control hardware that can be used to implement embodiments is not limiting. For example, embodiments described herein can be implemented in computer software using any suitable computer software language type, using, for example, conventional or object-oriented techniques. Such software can be stored on any type of suitable computer-readable medium or media, such as, for example, a magnetic or optical storage medium. The operation and behavior of the embodiments can be described without specific reference to specific software code or specialized hardware components. The absence of such specific references is feasible, because it is clearly understood that artisans of ordinary skill would be able to design software and control hardware to implement the embodiments based on the present description with no more than reasonable effort and without undue experimentation.

Moreover, the processes described herein can be executed by programmable equipment, such as computers or computer systems and/or processors. Software that can cause programmable equipment to execute processes can be stored in any storage device, such as, for example, a computer system (nonvolatile) memory, an optical disk, magnetic tape, or magnetic disk. Furthermore, at least some of the processes can be programmed when the computer system is manufactured or stored on various types of computer-readable media.

In various embodiments disclosed herein, a single component can be replaced by multiple components and multiple components can be replaced by a single component to perform a given function or functions. Except where such substitution would not be operative, such substitution is within the intended scope of the embodiments.

The foregoing description of embodiments and examples has been presented for purposes of illustration and description. It is not intended to be exhaustive or limiting to the forms described. Numerous modifications are possible in light of the above teachings. Some of those modifications have been discussed, and others will be understood by those skilled in the art. The embodiments were chosen and described in order to best illustrate principles of various embodiments as are suited to particular uses contemplated. The scope is, of course, not limited to the examples set forth herein, but can be employed in any number of applications and equivalent devices by those of ordinary skill in the art.

The invention claimed is:

1. A method of determining a nitrogen requirement for vegetation in a field, comprising:
   continuously measuring spectral reflectance received at a measuring device positioned proximate to the field, wherein the measuring device comprises a spectrometer measuring light in two or more wavelengths;
   based on the measured reflectance, determining a nitrogen level of a plant canopy of the field;
   based on the measured reflectance, determining a biomass of the plant canopy of the field; and
   based on the determined nitrogen level of the plant canopy and the biomass of the plant canopy, determining a nitrogen requirement of the vegetation.

2. The method of claim 1, wherein the nitrogen level of the canopy is estimated based on a spectral reflectance using a first vegetation index using a first and second wavelengths and an estimate of biomass, and
   wherein the biomass of the plant canopy is estimated based on the spectral reflectance using a second vegetation index using at least a third wavelength and an estimate of the nitrogen level of the canopy.

3. The method of claim 2, wherein the spectral reflectance is based on reflectance data collected from an airborne imager.

4. The method of claim 3, further comprising applying a correction factor to reflectance data.

5. The method of claim 4, wherein the correction factor is based on the reflectance data collected from the geographical coordinates of the radiation measuring device.

6. The method of claim 4, wherein the correction factor is based on a downwelling light spectrum collected within a scene of the airborne imager in comparison to a clear-sky spectrum.

7. The method of claim 3, wherein the airborne imager is a satellite.

8. The method of claim 2, where the first vegetation index is determined based solely upwelling radiation.

9. The method of claim 2, where the first vegetation index is determined based on a ratio of upwelling radiation to downwelling radiation.

10. The method of claim 2, further comprising estimating extraterrestrial radiation, wherein the measuring device comprises a pyranometer and a global positioning system (GPS).

11. The method of claim 10, further comprising, using data collected by the pyranometer and the GPS, estimating estimate solar angle and a fraction of actual radiation to potential radiation.

12. The method of claim 11, further comprising correcting a reflectance estimate for illumination conditions based on the estimated estimate solar angle and the fraction of actual radiation to potential radiation.

13. The method of claim 1, further comprising:
   estimating a rate of plant nitrogen uptake from the soil based on sequential measurements.

14. The method of claim 1, further comprising:
   estimating a rate of nitrogen translocation from leaves to other organs.

15. The method of claim 14, further comprising:
   estimating any of nitrogen content and protein content of a harvested biomass using the estimated rate of nitrogen translocation.

16. A system, comprising:
   a measuring device, comprising:
      a spectrometer configured to measure two or more wavelengths of shortwave radiation;
      a control unit electrically coupled to the spectrometer, wherein the control unit is configured to:
         continuously measure spectral reflectance received at the measuring device positioned proximate to the field, wherein the measuring device comprises a spectrometer measuring light in two or more wavelengths;
         based on the measured reflectance, determine a nitrogen level of a plant canopy of vegetation planted in the field;
         based on the measured reflectance, determine a biomass of the plant canopy of vegetation planted in the field; and
         based on the determined nitrogen level of the plant canopy and the biomass of the plant canopy, determine a nitrogen requirement of the vegetation planted in the field.

17. The system of claim 16, wherein the nitrogen level of the canopy is estimated based on a spectral reflectance using a first vegetation index using a first and second wavelengths and an estimate of biomass, and
   wherein the biomass of the plant canopy is estimated based on the spectral reflectance using a second vegetation index using at least a third wavelength and an estimate of the nitrogen level of the canopy.

18. The system of claim 17, wherein the spectral reflectance is based on reflectance data collected from an airborne imager.

19. The system of claim 18, wherein the control unit is configured to apply a correction factor to reflectance data.

20. The system of claim 19, wherein the correction factor is based on the reflectance data collected from the geographical coordinates of the radiation measuring device.

21. The system of claim 19, wherein the correction factor is based on a downwelling light spectrum collected within a scene of the airborne imager in comparison to a clear-sky spectrum.

22. The system of claim 16, wherein the control unit is configured to estimate a rate of plant nitrogen uptake from the soil based on sequential measurements.

23. The system of claim 16, wherein the control unit is configured to estimate a rate of nitrogen translocation from leaves to other organs.

24. The system of claim 23, wherein the control unit is configured to estimate any of nitrogen content and protein content of a harvested biomass using the estimated rate of nitrogen translocation.

\* \* \* \* \*